(12) United States Patent
Pschirer et al.

(10) Patent No.: US 7,858,636 B2
(45) Date of Patent: Dec. 28, 2010

(54) HEXARYLENE AND PENTARYLENE TETRACARBOXYLIC ACID DIIMIDES

(75) Inventors: Neil Gregory Pschirer, Mainz (DE); Christopher Kohl, Mainz (DE); Klaus Muellen, Cologne (DE)

(73) Assignees: BASF Aktiengesellschaft, Ludwigshafen (DE); Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 697 days.

(21) Appl. No.: 11/910,944

(22) PCT Filed: Apr. 13, 2006

(86) PCT No.: PCT/EP2006/061603
§ 371 (c)(1),
(2), (4) Date: Oct. 8, 2007

(87) PCT Pub. No.: WO2006/111511
PCT Pub. Date: Oct. 26, 2006

(65) Prior Publication Data
US 2008/0188660 A1    Aug. 7, 2008

(30) Foreign Application Priority Data
Apr. 19, 2005    (DE)    .................... 10 2005 018 241

(51) Int. Cl.
A61K 31/4375    (2006.01)
C07D 221/18    (2006.01)
C07F 5/02    (2006.01)

(52) U.S. Cl. .................... 514/279; 546/13; 546/26

(58) Field of Classification Search ................ 514/279; 546/13, 26
See application file for complete search history.

(56) References Cited

U.S. PATENT DOCUMENTS

| 5,405,962 | A | 4/1995 | Muellen et al. |
| 5,986,099 | A | 11/1999 | Mullen et al. |
| 6,124,458 | A | 9/2000 | Muellen et al. |

FOREIGN PATENT DOCUMENTS

| EP | 0 596 292 B1 | 5/1994 |
| EP | 0 804 507 B1 | 11/1997 |
| WO | WO 96/22332 | 7/1996 |
| WO | WO 02/077081 A1 | 10/2002 |

OTHER PUBLICATIONS

Christopher Kohl, et al., "Bis(Rylenedicarboximide)-a,d-1,5-Diaminoanthraquinones As Unique Infrared Absorbing Dyes", Journal of the Royal Society of Chemistry, XP-002256670, 2002, pp. 2778 and 2779.

Heribert Quante, et al., "Quaterrylenebis(Dicarboximides)", Angewandte Chemie, XP 002002793, vol. 34, No. 12, Jul. 7, 1995, pp. 1323-1325.

Primary Examiner—Taofiq A Solola
(74) Attorney, Agent, or Firm—Oblon, Spivak, McClelland, Maier & Neustadt, L.L.P.

(57) ABSTRACT

Rylenetetracarboximides of the general formula I

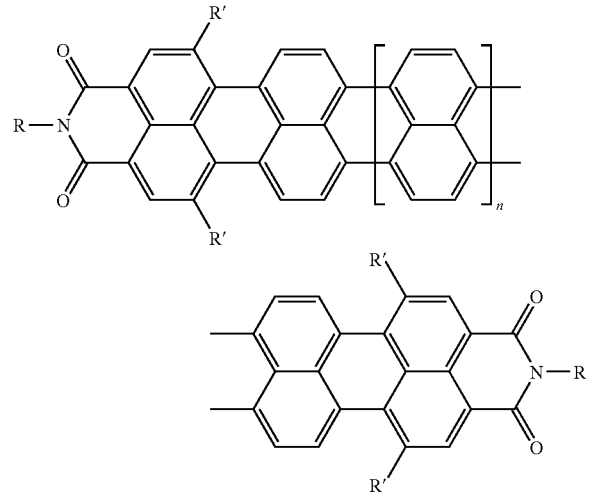

in which the variables are defined as follows:
R are identical or different radicals: hydrogen; alkyl, cycloalkyl, aryl or hetaryl, each substituted if desired;
R' are identical or different radicals: hydrogen; aryloxy, arylthio, hetaryloxy or hetarylthio, each substituted if desired;
n is 1 or 2,
and also a process for preparing the rylenetetracarboximides I and their use for coloring high molecular weight organic and inorganic materials, for preparing aqueous polymer dispersions which absorb in the near infrared region of the electromagnetic spectrum, for producing markings and inscriptions which absorb infrared light and are invisible to the human eye, as infrared absorbers for heat management, as IR laser beam-absorbing materials in fusion treatment of plastics parts, and also as active components in photovoltaics.

29 Claims, No Drawings

HEXARYLENE AND PENTARYLENE TETRACARBOXYLIC ACID DIIMIDES

CROSS-REFERENCE TO RELATED APPLICATIONS

The present application is a 35 U.S.C. §371 National Stage patent application of International patent application PCT/EP06/061603, filed on Apr. 13, 2006, which claims priority to German patent application DE 102005018241.0, filed on Apr. 19, 2005.

The present invention relates to novel rylenetetracarboximides of the general formula I

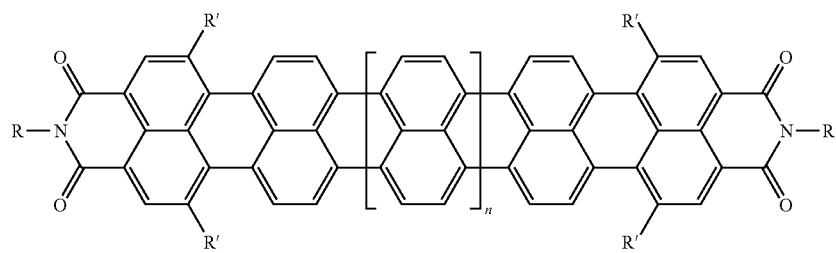

in which the variables are defined as follows:

R are identical or different radicals:

hydrogen;

$C_1$-$C_{30}$-alkyl whose carbon chain may be interrupted by one or more —O—, —S—, —$NR^1$—, —CO— and/or —$SO_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may comprise further heteroatoms and be aromatic;

$C_5$-$C_8$-cycloalkyl whose carbon skeleton may be interrupted by one or more —O—, —S— and/or —$NR^1$— moieties and/or which may be mono- or polysubstituted by $C_1$-$C_{18}$-alkyl;

aryl or hetaryl, each of which may be mono- or polysubstituted by $C_1$-$C_{18}$-alkyl, $C_1$-$C_{18}$-alkoxy, cyano, nitro, halogen, —$NR^2R^3$, —$CONR^2R^3$, —$SO_2R^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —$NR^1$—, —CO— and/or —$SO_2$— as ring members and/or be substituted by one or more identical or different $R^2$ radicals;

R' are identical or different radicals:

hydrogen;

aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —$COOR^1$, —$CONR^2R^3$ and/or —$NHCOR^2$;

$R^1$ is hydrogen or $C_1$-$C_{18}$-alkyl;

$R^2$, $R^3$ are each independently hydrogen;

$C_1$-$C_{18}$-alkyl, which may be substituted by $C_1$-$C_6$-alkoxy, halogen, hydroxyl, carboxyl and/or cyano; aryl or hetaryl, each of which may be substituted by the aforementioned radicals specified for alkyl and by $C_1$-$C_6$-alkyl;

n is 1 or 2, and to their preparation and to their use for coloring high molecular weight organic and inorganic materials, for preparing aqueous polymer dispersions which absorb in the near infrared region of the electromagnetic spectrum, for the production of markings and inscriptions which absorb infrared light and are invisible to the human eye, as infrared absorbers for heat management, as IR laser beam-absorbing materials in fusion treatment of plastics parts, and as active components in photovoltaics.

The invention further relates, as intermediates for the rylenetetracarboximides I (unless stated otherwise, R and R' in the following formulae are each as defined above), to novel bisterrylene derivatives of the general formula VII

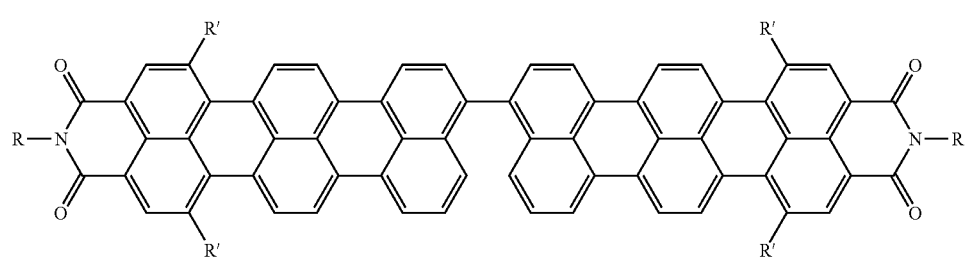

to novel 11-(9-perylene-3,4-dicarboximide)terrylene-3,4-dicarboximides of the general formula VIII together to form a five-membered ring which comprises the two oxygen atoms and the boron atom and

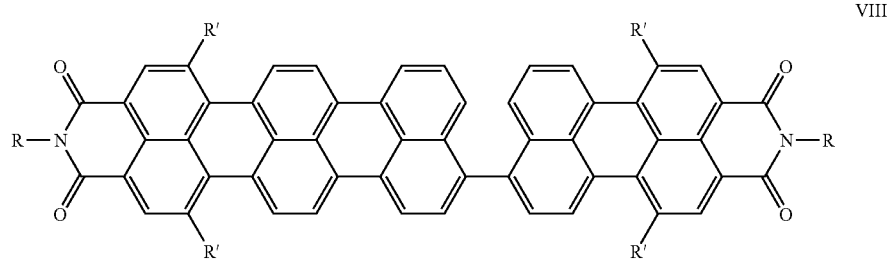

VIII to novel terrylene-3,4-dicarboximides of the general formula VI

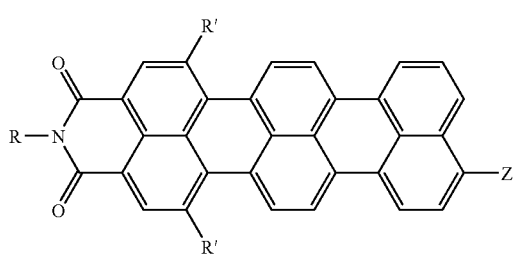

VI where
Z is bromine, iodine, amino, nitro or a radical

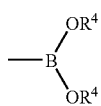

$R^4$ are identical or different radicals:

hydrogen, $C_1$-$C_{30}$-alkyl, $C_5$-$C_8$-cycloalkyl, aryl or hetaryl, where the two $R^4$ radicals may also be joined may be substituted on the carbon atoms by up to 4 $C_1$-$C_{30}$-alkyl, $C_5$-$C_8$-cycloalkyl, aryl or hetaryl groups, R' is not hydrogen, to novel 9-(5-nitronaphthyl)perylene-3,4-dicarboximides of the general formula V

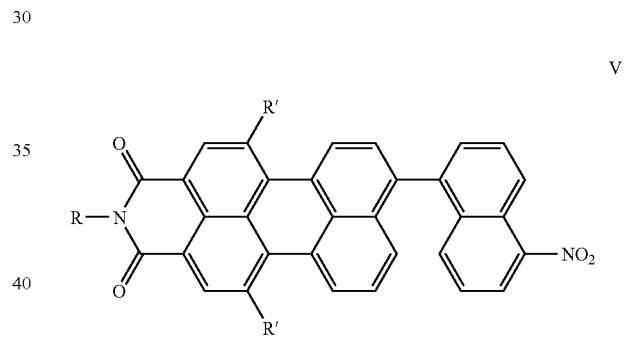

V where R' is not hydrogen,
to novel 13-(9-perylene-3,4-dicarboximide)quaterrylene-3,4-dicarboximides of the general formula XI

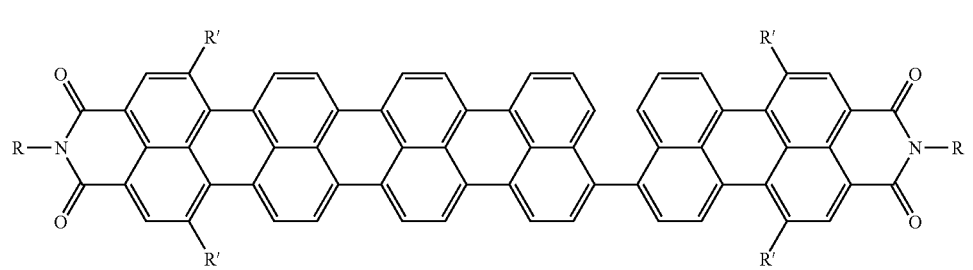

XI to novel perylene-3,9-bis(perylene-3,4-dicarboximides) of the general formula Xa
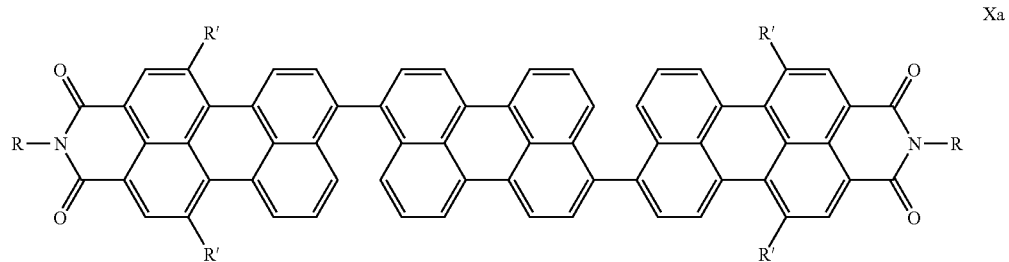
to novel perylene-3,10-bis(perylene-3,4-dicarboximides) of the general formula Xb
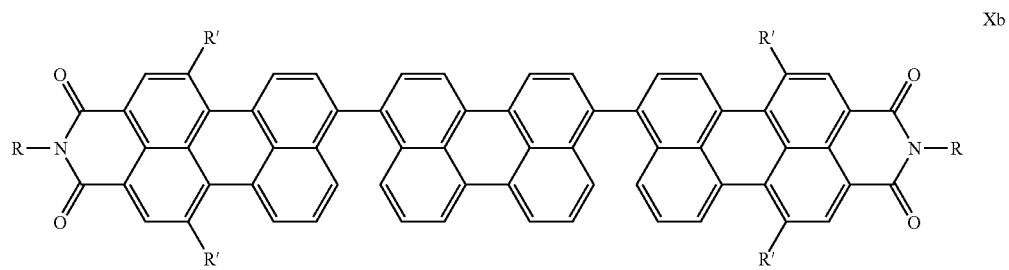
to novel bis(dioxaborolan-2-yl)perylenes of the general formula IXb
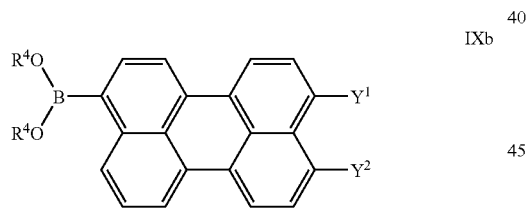
to novel naphthalene-1,5-bis(perylene-3,4-dicarboximides) of the general formula XIIa
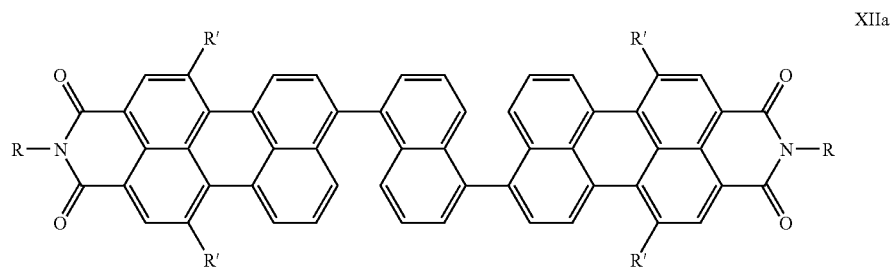

and to novel naphthalene-1,4-bis(perylene-3,4-dicarboximides) of the general formula XIIb

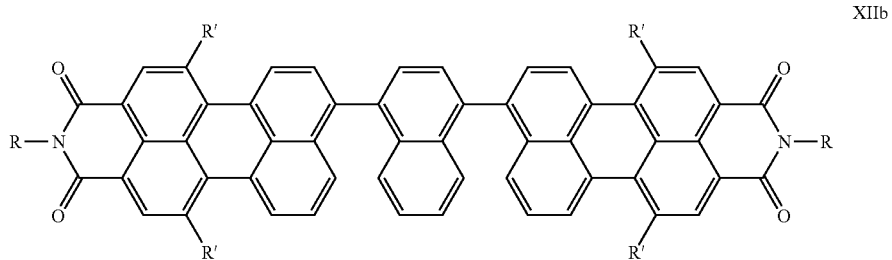

Higher rylenetetracarboximides are known to be of particular interest for applications owing to their strong absorption in the near infrared region of the electromagnetic spectrum. For example, WO-A-02/77081 describes the use of quaterrylene-tetracarboximides as infrared absorbers for thermal protection in glass laminates.

Quaterrylenetetracarboximides have the largest fused ring system known to date.

It was an object of the invention to provide compounds whose absorption lies in a region of the electromagnetic spectrum which is at an even longer wave length than the region accessible with the rylenetetracarboximides known to date.

Accordingly, the rylenetetracarboximides of the formula I defined at the outset, specifically the hexarylenetetracarboximides of the formula Ia Preferred ryleneimides I can be taken from the subclaim.

Additionally found has been a process for preparing the hexarylenetetracarboximides of the formula Ia in which R' is not hydrogen (referred to hereinbelow as "process A1-hexarylene"), which comprises a) reacting a diborane of the general formula II

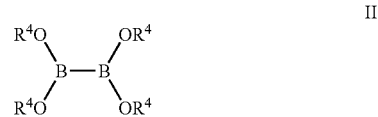

in which the $R^4$ radicals are each as defined above,

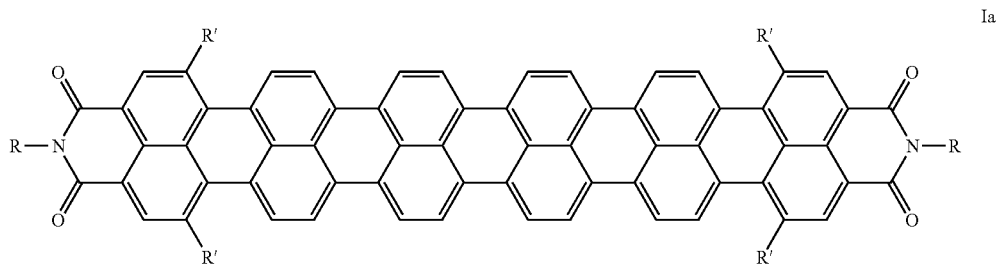

and the pentarylenetetracarboximides of the formula Ib

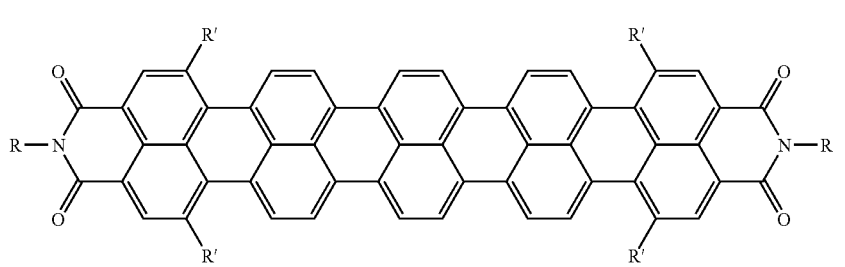

have been found.

in the presence of an aprotic organic solvent, of a transition metal catalyst and of a base with a1) a 9-bromoperylene-3,4-dicarboximide of the general formula IIIa

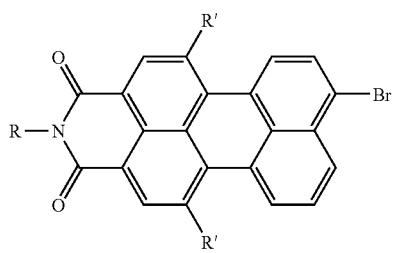

IIIa or a2) a naphthalene derivative of the general formula IIIb

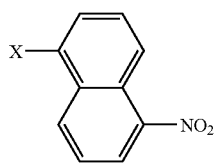

IIIb in which X is halogen, $C_1$-$C_{12}$-alkylsulfonyl, whose alkyl radical may be mono- or polysubstituted by halogen, or $C_6$-$C_{18}$-arylsulfonyl, b1) subjecting the 9-(dioxaborolan-2-yl)perylene-3,4-dicarboximide of the general formula IVa

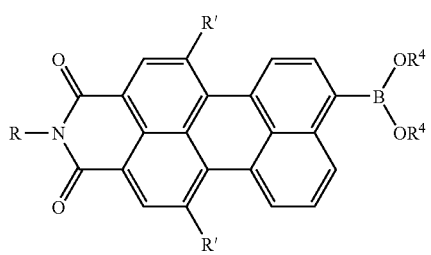

IVa formed in step a1), in the presence of an organic solvent, if desired in a mixture with water, and of a transition metal catalyst and of a base, to a Suzuki coupling reaction with a naphthalene derivative IIIb or b2) subjecting the 1-(dioxaborolan-2-yl)-5-nitronaphthalene of the general for formula IVb

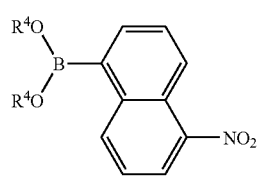

IVb formed in step a2), in the presence of an organic solvent, if desired in a mixture with water, and of a transition metal catalyst and of a base, to a Suzuki coupling reaction with a 9-bromoperylene-3,4-dicarboximide IIIa, c) subjecting the 9-(5-nitronaphthyl)perylene-3,4-dicarboximide of the general formula V

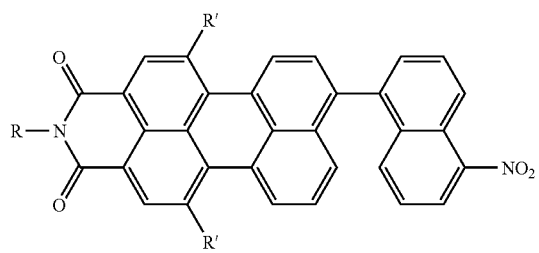

V formed in step b1) or b2) to a cyclodehydrogenation in the presence of a base-stable, high-boiling organic solvent and of an alkali metal- or alkaline earth metal-containing base and of a nitrogen-containing auxiliary base, d) reducing the 11-nitroterrylene-3,4-dicarboximide of the general formula VIa

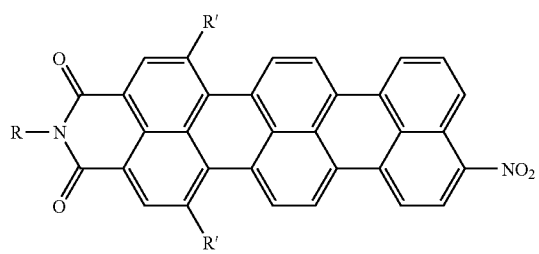

VIa formed in step c) with nascent hydrogen, e) diazotizing the 11-aminoterrylene-3,4-dicarboximide of the general formula VIb

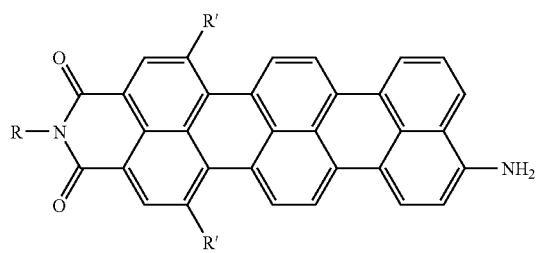

VIb formed in step d) and reacting the diazonium salt formed with a metal bromide or iodide, f) coupling the 11-haloterrylene-3,4-dicarboximide of the general formula VIc

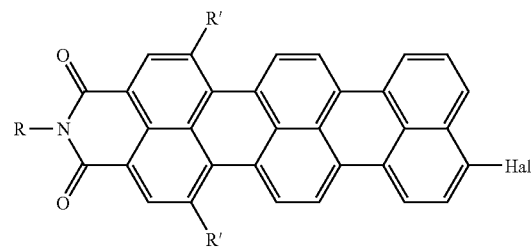

VIc in which Hal is bromine or iodine, formed in step e), f1) in the presence of an organic transition metal complex as a catalyst, of free ligand molecules and of an aprotic solvent to give a bisterrylene derivative of the general formula VII

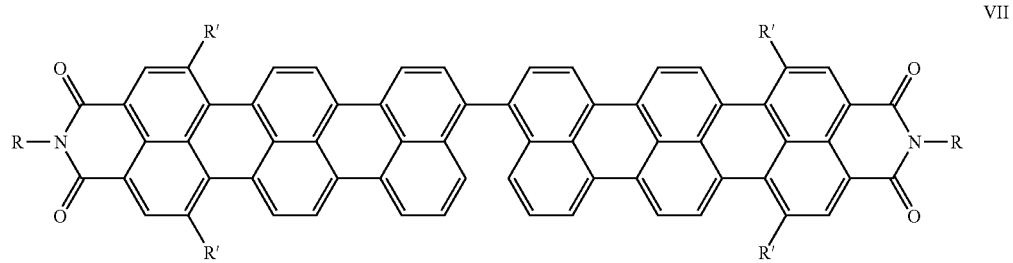

VII or f2) in the presence of from 30 to 70 mol %, based on the 11-haloterrylene-3,4-dicarboximide VIc, of a diborane II, of a transition metal catalyst, of a base and of an aprotic organic solvent, without intermediate isolation of the 11-(dioxaborolan-2-yl)terrylene-3,4-dicarboximide of the general formula VId

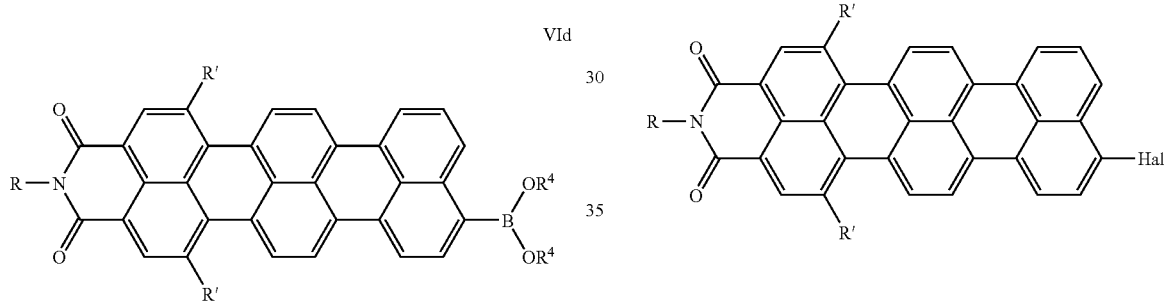

VId formed in situ, converting it by a Suzuki coupling reaction to the bisterrylene derivative VII and g) converting the bisterrylene derivative VII by cyclodehydrogenation, g1) in an organic reaction medium having hydroxyl and amino functions and comprising a substantially undissolved base or g2) in the presence of a base-stable, high-boiling organic solvent and of an alkali metal- or alkaline earth metal-containing base and of a nitrogen-containing auxiliary base, to the hexarylenetetracarboximide Ia.

Also found has been a process for preparing the hexarylenetetracarboximides of the formula Ia in which R' is not hydrogen (referred to hereinbelow as "process A2-hexarylene"), which comprises a) reacting a diborane of the general formula II

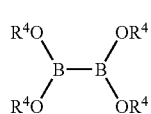

II in which the R⁴ radicals are each as defined above, in the presence of an aprotic organic solvent, of a transition metal catalyst and of a base with 11-haloterrylene-3,4-dicarboximide of the general formula VIc

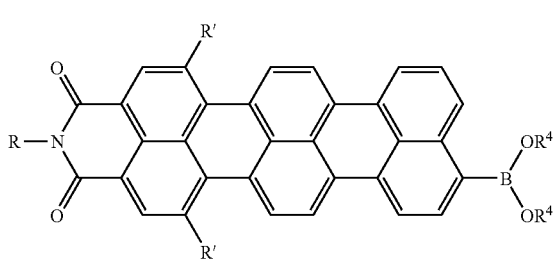

VIc in which Hal is bromine or iodine, b) subjecting the 11-(dioxaborolan-2-yl)terrylene-3,4-dicarboximide of the general formula VId VId formed in step a), in the presence of an organic solvent, if desired in a mixture with water, and of a transition metal catalyst and of a base, to a Suzuki coupling reaction with an 11-haloterrylene-3,4-dicarboximide VIc and c) converting the bisterrylene derivative of the general formula VII

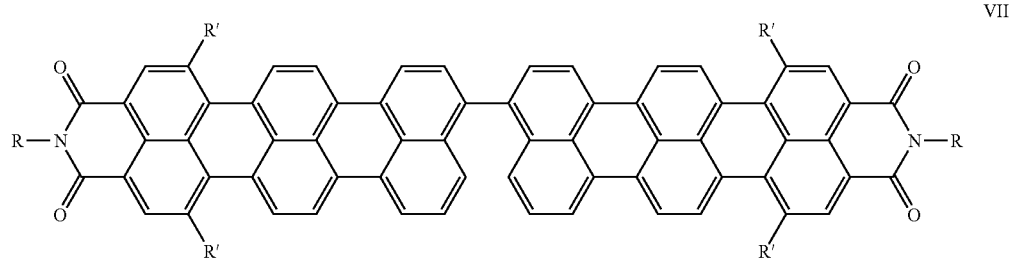

VII formed in step b) by cyclodehydrogenation,
c1) in an organic reaction medium having hydroxyl and amino functions and comprising a substantially undissolved base
or
c2) in the presence of a base-stable, high-boiling organic solvent and of an alkali metal- or alkaline earth metal-containing base and of a nitrogen-containing auxiliary base,
to the hexarylenetetracarboximide Ia.

Additionally found has been a process for preparing the pentarylenetetracarboximides of the formula Ib, in which R' is not hydrogen (referred to hereinbelow as "process A1-pentarylene"), which comprises
a) subjecting the 11-haloterrylene-3,4-dicarboximide of the general formula VIc

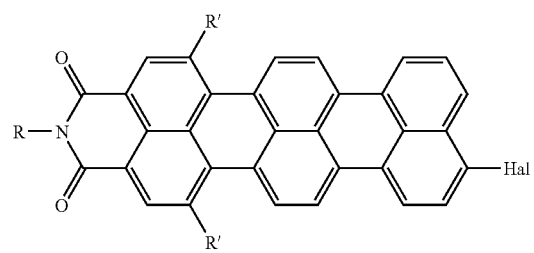

VIc in the presence of an organic solvent, if desired in a mixture with water, and also of a transition metal catalyst and of a base, to a Suzuki coupling reaction with a 9-(dioxaborolan-2-yl)perylene-3,4-dicarboximide of the general formula IVa

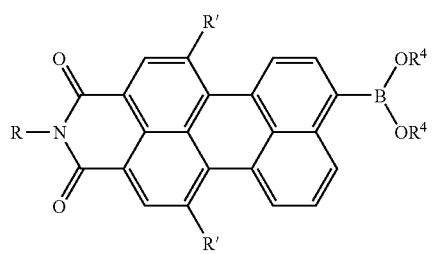

IVa and b) converting the 11-(9-perylene-3,4-dicarboximide)terrylene-3,4-dicarboximide of the general formula VIII

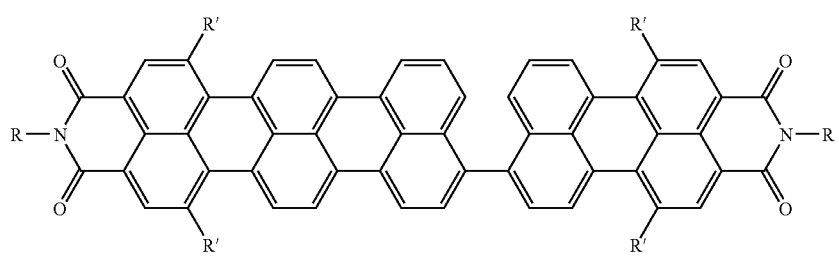

VIII formed in step a) by cyclodehydrogenation, b1) in an organic reaction medium having hydroxyl and amino functions and comprising a substantially undissolved base or b2) in the presence of a base-stable, high-boiling organic solvent and of an alkali metal- or alkaline earth metal-containing base and of a nitrogen-containing auxiliary base, to the pentarylenetetracarboximide Ib.

Additionally found has been a process for preparing pentarylenetetracarboximides of the formula Ib in which R' is not hydrogen (referred to hereinbelow as "process A2-pentarylene"), which comprises a) subjecting an 11-(dioxaborolan-2-yl)terrylene-3,4-dicarboximide of the general formula VId VId

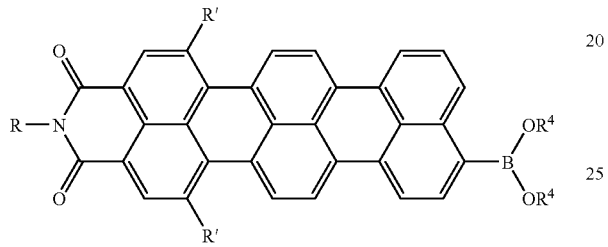

in the presence of an organic solvent, if desired in a mixture with water, and also of a transition metal catalyst and of a base, to a Suzuki coupling reaction with a 9-bromoperylene-3,4-dicarboximide of the general formula IIIa IIIa

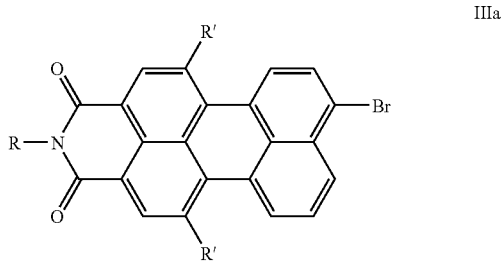

and b) converting the 11-(9-perylene-3,4-dicarboximide)terrylene-3,4-dicarboximide of the general formula VIII

VIII

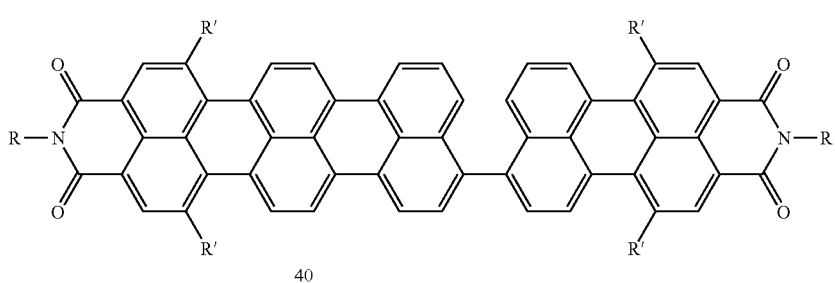

formed in step a) by cyclodehydrogenation, b1) in an organic reaction medium having hydroxyl and amino functions and comprising a substantially undissolved base or b2) in the presence of a base-stable, high-boiling organic solvent and of an alkali metal- or alkaline earth metal-containing base and of a nitrogen-containing auxiliary base, to the pentarylenetetracarboximide Ib.

Also found have been the bisterrylene derivatives, occurring as intermediates in process A, of the formula VII defined at the outset

VII

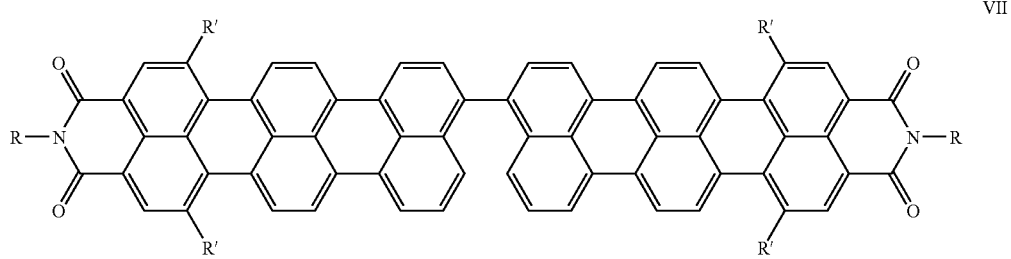

the 11-(9-perylene-3,4-dicarboximide)terrylene-3,4-dicarboximides of the formula VIII defined at the outset

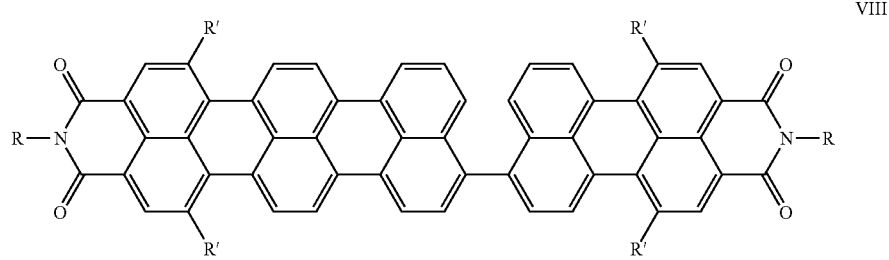

VIII the terrylene-3,4-dicarboximides of the formula VI defined at the outset

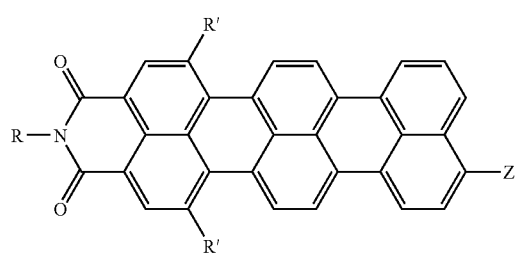

VI and the 9-(5-nitronaphthyl)perylene-3,4-dicarboximides of the formula V defined at the outset

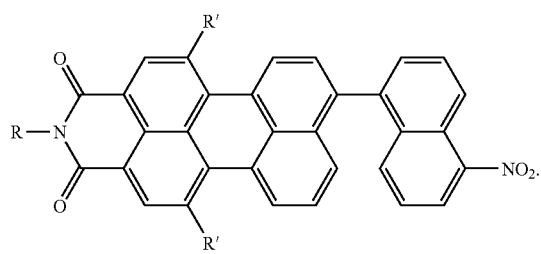

V

Finally, a further process has been found for preparing the hexarylenetetracarboximides Ia (referred to hereinbelow as "process B-hexarylene"), which comprises a) reacting a diborane of the general formula II

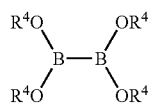

II in the presence of an aprotic organic solvent, of a transition metal catalyst and of a base with a1) a 9-bromoperylene-3,4-dicarboximide of the general formula IIIa

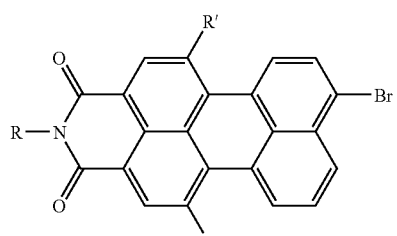

IIIa or a2) a dihaloperylene of the general formula IXa

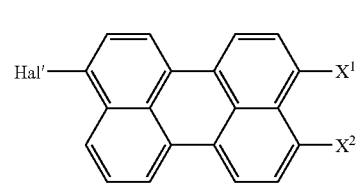

IXa in which Hal' is chlorine or bromine and one of the two $X^1$ and $X^2$ radicals is likewise Hal' and the other radical is hydrogen, b1) subjecting the 9-(dioxaborolan-2-yl)perylene-3,4-dicarboximide of the general formula IVa

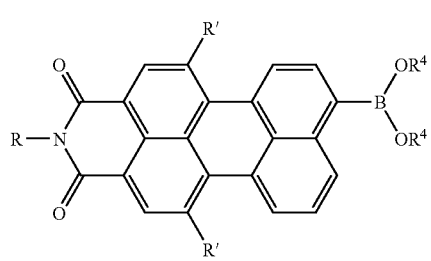

IVa formed in step a1), in the presence of an organic solvent, if desired in a mixture with water, and of a transition metal catalyst and of a base, to a Suzuki coupling reaction with a dihaloperylene IXa in a molar ratio of from 2:1 to 6:1 or b2) subjecting the bis(dioxaborolan-2-yl)perylene of the general formula IXb

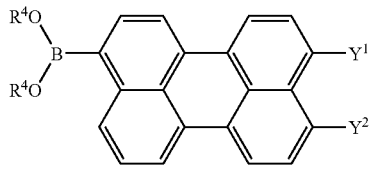

IXb formed in step a2), in which one of the two $Y^1$ and $Y^2$ radicals is likewise a radical

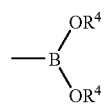

and the other radical is hydrogen, in the presence of an organic solvent, if desired in a mixture with water, and also of a transition metal catalyst and of a base, to a Suzuki coupling reaction with a 9-bromoperylene-3,4-dicarboximide IIIa in a molar ratio of from 1:2 to 1:6 and c) subjecting the perylene-3,9-bis(perylene-3,4-dicarboximide) of the general formula Xa

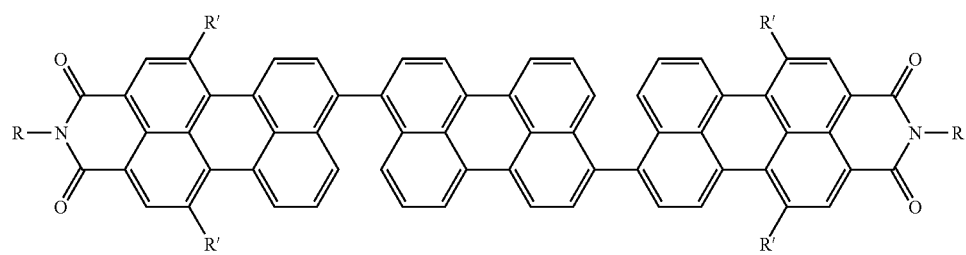

Xa or perylene-3,10-bis(perylene-3,4-dicarboximide) of the general formula Xb

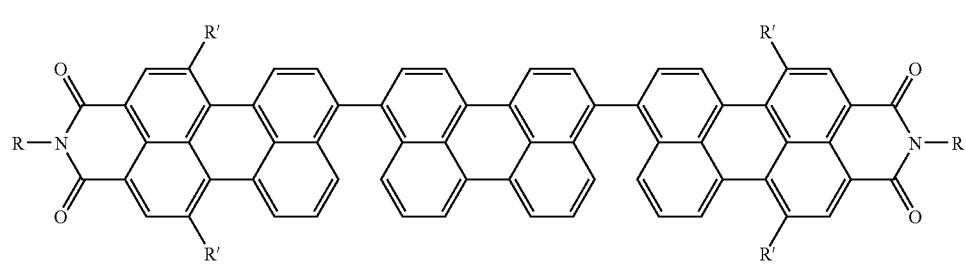

Xb formed in step b1) or b2)

c1) to a one-stage cyclodehydrogenation in the presence of a strong Lewis acid and of an inert organic solvent directly to give the hexarylenetetracarboximide Ia or c2a) contacting it with a weak Lewis acid in a first step at room temperature in the presence of an inert organic solvent and c2b) then, after intermediate isolation, in a second step, further cyclodehydrogenating the thus formed 13-(9-perylene-3,4-dicarboximide)quaterrylene-3,4-dicarboximide of the general formula XI

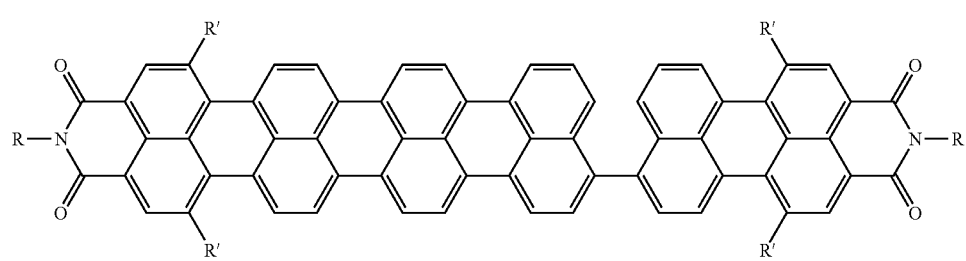

XI c2bα) in an organic reaction medium having hydroxyl and amino functions and comprising a substantially undissolved base or c2bβ) in the presence of a base-stable, high-boiling organic solvent and of an alkali metal- or alkaline earth metal-containing base and of a nitrogen-containing auxiliary base to the hexarylenetetracarboximide Ia.

Also found has been a process, analogous to the former process, for preparing the pentarylenetetracarboximides Ib (referred to hereinbelow as "process B-pentarylene"), which comprises a) reacting a diborane of the general formula II

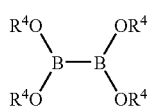

II in the presence of an aprotic organic solvent, of a transition metal catalyst and of a base with a1) a 9-bromoperylene-3,4-dicarboximide of the general formula IIIa

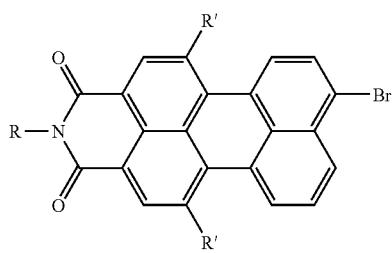

IIIa or
a2) a dihalonaphthalene of the general formula IXc

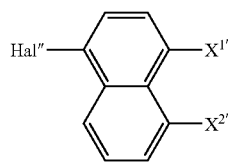

IXc in which Hal" is chlorine, bromine or iodine and one of the two $X^{1'}$ and $X^{2'}$ radicals is likewise Hal" and the other radical is hydrogen, b1) subjecting the 9-(dioxaborolan-2-yl)perylene-3,4-dicarboximide of the general formula IVa

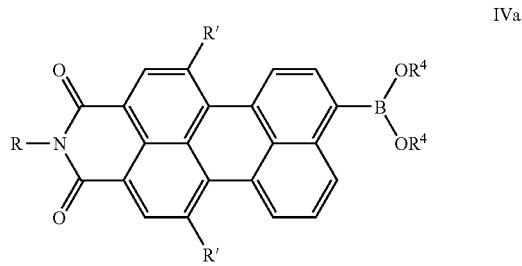

IVa formed in step a1), in the presence of an organic solvent, if desired in a mixture with water, and of a transition metal catalyst and of a base, to a Suzuki coupling reaction with a dihalonaphthalene IXc in a molar ratio of from 2:1 to 6:1 or b2) subjecting the bis(dioxaborolan-2-yl)naphthalene of the general formula IXd

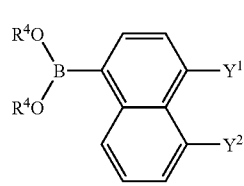

IXd formed in step a2), in which one of the two $Y^1$ and $Y^2$ radicals is likewise a radical

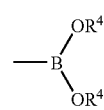

and the other radical is hydrogen,
in the presence of an organic solvent, if desired in a mixture with water, and also of a transition metal catalyst and of a base, to a Suzuki coupling reaction with a 9-bromoperylene-3,4-dicarboximide IIIa in a molar ratio of from 1:2 to 1:6 and c) subjecting the naphthalene-1,5-bis(perylene-3,4-dicarboximide) of the general formula XIIa

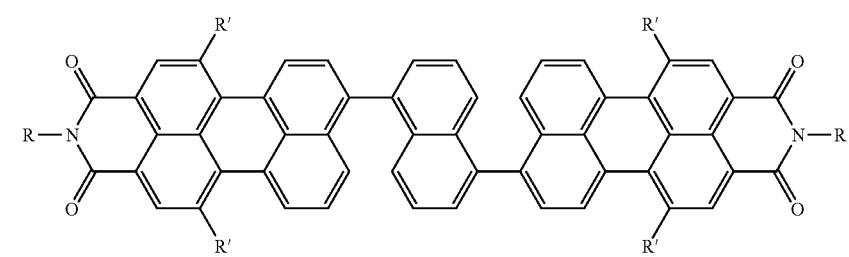

XIIa or naphthalene-1,4-bis(perylene-3,4-dicarboximide) of the general formula XIIb

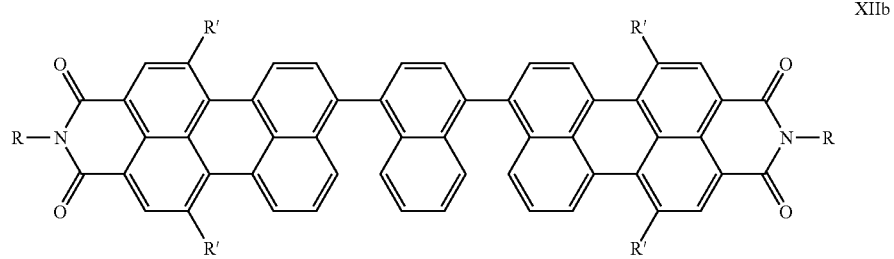

XIIb formed in step b1) or b2)
c1) to a one-stage cyclodehydrogenation in the presence of a strong Lewis acid and of an inert organic solvent directly to give the pentarylenetetracarboximide Ib or
c2a) contacting it with a weak Lewis acid in a first step at room temperature in the presence of an inert organic solvent and
c2b) then, after intermediate isolation, in a second step, further cyclodehydrogenating the thus formed 11-(9-perylene-3,4-dicarboximide)terylene-3,4-dicarboximide of the general formula VIII c2bβ) in the presence of a base-stable, high-boiling organic solvent and of an alkali metal- or alkaline earth metal-containing base and of a nitrogen-containing auxiliary base to the pentarylenetetracarboximide Ib.

Also found have been the 13-(9-perylene-3,4-dicarboximide)quaterrylene-3,4-dicarboximides, occurring as intermediates in process B, of the formula XI defined at the outset

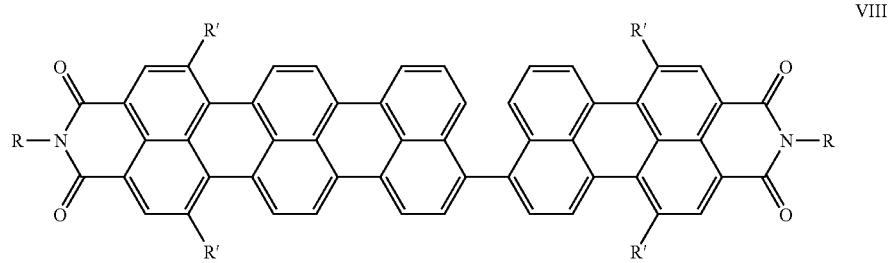

VIII c2bα) in an organic reaction medium having hydroxyl and amino functions and comprising a substantially undissolved base or

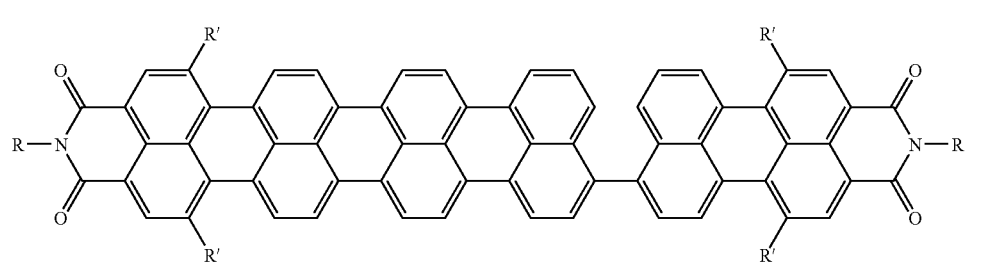

XI the perylene-3,9-bis(perylene-3,4-dicarboximides) of the formula Xa defined at the outset
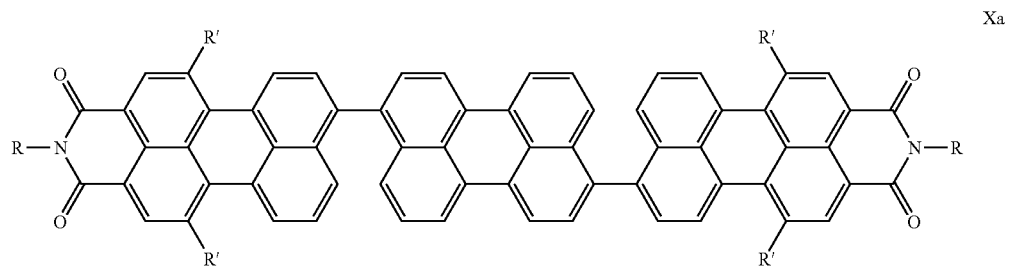
Xa
the perylene-3,10-bis(perylene-3,4-dicarboximides) of the formula Xb defined at the outset
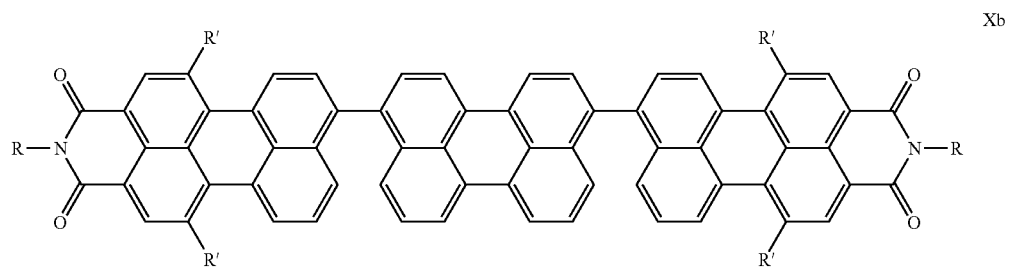
Xb
the bis(dioxaborolan-2-yl)perylenes of the formula IXb defined at the outset
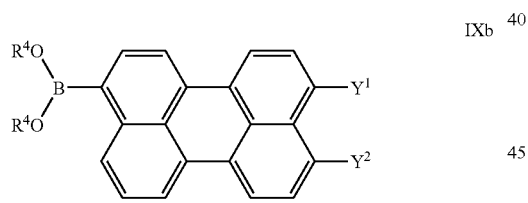
IXb
the naphthalene-1,5-bis(perylene-3,4-dicarboximides) of the formula XIIa defined at the outset
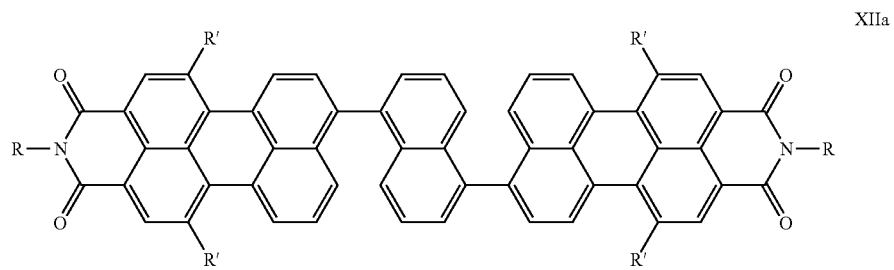
XIIa and the naphthalene-1,4-bis(perylene-3,4-dicarboximides) of the formula XIIb defined at the outset

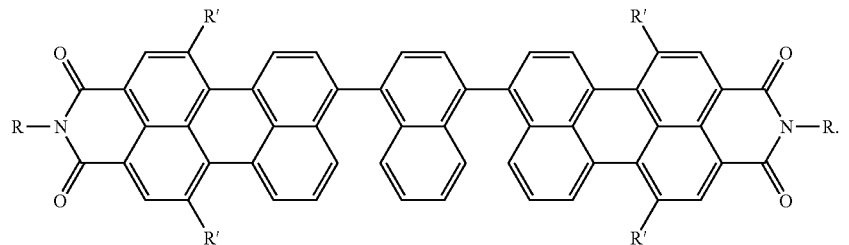

Finally, the use has been found of rylenetetracarboximides I for coloring high molecular weight organic and inorganic materials, for preparing aqueous polymer dispersions which absorb in the near infrared region of the electromagnetic spectrum, for producing markings and inscriptions which absorb infrared light and are invisible to the human eye, as infrared absorbers for heat management, as IR laser beam-absorbing materials in fusion treatment of plastics parts, and also as active components in photovoltaics.

Specific examples of the R, R', $R^1$ to $R^5$ radicals mentioned in the formulae and their substituents are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetra-oxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethyl-thiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-tri-thiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethyl-aminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-di-azaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-4-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonyl-ethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonyl-butyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclo-pentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthyl-azo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The preparation processes according to the invention are illustrated in detail hereinbelow.

Process A1-Hexarylene:

Step a)—Process A1-Hexarylene:

In the inventive process A1 for preparing the hexarylenetetracarboximides Ia (het)aryloxy- and (het)arylthio-substituted on the rylene ring, a diborane II is reacted in step a) with a1) a 9-bromoperylene-3,4-dicarboximide IIIa or a2) a 1,5-disubstituted naphthalene derivative IIIb. The naphthalene derivative IIIb bears an X radical (halogen atom or alkyl- or arylsulfonyl radical) which can react with the diborane II, and also a nitro group which enables the subsequent reactions of the terrylene-3,4-dicarboximide formed in step d).

9-Bromoperylene-3,4-dicarboximide IIIa and naphthalene derivative IIIb are referred to together hereinbelow as "reactant III".

The reaction of the diborane II with the reactant III is undertaken in the presence of an aprotic organic solvent, of a transition metal catalyst and of a base.

The molar ratio of diborane II to reactant III is generally from 0.8:1 to 3:1, in particular from 1.5:1 to 2:1.

Suitable solvents for step a) are in principle all aprotic solvents which are stable against bases under the reaction conditions and have a boiling point above the selected reaction temperature, in which the reactants III dissolve fully at reaction temperature and the catalysts and bases used at least partially, so that the reaction conditions are substantially homogeneous. It is possible to use either nonpolar-aprotic or polar-aprotic solvents, preference being given to the nonpolar-aprotic solvents.

Examples of preferred nonpolar-aprotic solvents are solvents which boil at >100° C. from the following groups: aliphates (especially $C_8$-$C_{18}$-alkanes), unsubstituted, alkyl-substituted and fused cycloaliphates (especially unsubstituted $C_7$-$C_{10}$-cycloalkanes, $C_6$-$C_8$-cycloalkanes, which have been substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or one $C_5$-$C_8$-cycloalkyl radical) and fused aromatics which may be alkyl-substituted and/or partly hydrogenated (especially naphthalene which has been substituted by from one to four $C_1$-$C_6$-alkyl groups), and also mixtures of these solvents.

Specific examples of particularly preferred solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methyl-cycloheptane and methylcyclooctane; toluene, o-, m-und p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as are obtainable from the high-boiling, partly or fully hydrogenated fractions from thermal and catalytic cracking processes in crude oil or naphtha processing, for example mixtures of the Exxsol® type and alkylbenzene mixtures of the Solvesso® type.

Very particularly preferred solvents are xylene (all isomers), mesitylene and in particular toluene.

Examples of suitable polar-aprotic solvents are N,N-disubstituted aliphatic carboximides (especially N,N-di-$C_1$-$C_4$-alkyl-$C_1$-$C_4$-carboximides), nitrogen heterocycles and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Specific examples of particularly suitable solvents include: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; tetrahydrofuran, dioxane, diphenyl ether, diethylene glycol dimethyl, diethyl, dipropyl, diisopropyl, di-n-butyl, di-sec-butyl and di-tert-butyl ether, diethylene glycol methyl ethyl ether, triethylene glycol dimethyl and diethyl ether and triethylene glycol methyl ethyl ether.

In the case of the reactants IIIa, particular preference is given to the nonpolar-aprotic solvents, in particular toluene; in the case of the reactants IIIb, particular preference is given to polar-aprotic solvents, especially dioxane.

The amount of solvents is generally from 10 to 1000 ml, preferably from 20 to 300 ml, per g of reactant III.

Suitable transition metal catalysts are in particular palladium complexes such as tetrakis(triphenylphosphine)palladium(0), tetrakis(tris-o-tolylphosphine)palladium(0), [1,2-bis(diphenylphosphino)ethane]palladium(II) chloride, [1,1'-bis(diphenylphosphino)-ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium(0), 1,5-cyclooctadienepalladium(II) chloride, bis(acetonitrile)palladium(II) chloride and bis(benzonitrile)palladium(II) chloride, preference being given to [1,1'-bis(diphenylphosphino)ferrocene]palladium(II) chloride and tetrakis(triphenylphosphine)palladium(0).

Typically, the transition metal catalyst is used in an amount of from 1 to 20 mol %, in particular from 2 to 10 mol %, based on the reactant III.

The bases used are preferably the alkali metal salts, especially the sodium and in particular the potassium salts, weak organic and inorganic acids such as sodium acetate, potassium acetate, sodium carbonate, sodium hydrogencarbonate, potassium carbonate and potassium hydrogencarbonate. Preferred bases are the acetates, in particular potassium acetate.

In general, from 1 to 5 mol, preferably from 2 to 4 mol, of base are used per mole of reactant III.

The reaction temperature is typically from 20 to 180° C., in particular from 60 to 120° C.

The reaction time is generally from 0.5 to 30 h, in particular from 1 to 20 h.

In process technology terms, the procedure in step a) is appropriately as follows:

Reactant III and solvent are initially charged, the transition metal catalyst and the base are added successively and the mixture is heated to the desired reaction temperature under protective gas for from 0.5 to 30 h. After cooling to room temperature, the solid constituents are filtered out of the reaction mixture and the solvent is distilled off under reduced pressure.

The purity of the thus prepared 9-(dioxaborolan-2-yl)perylene-3,4-dicarboximide IVa or 1-(dioxaborolan-2-yl)-5-nitronaphthalene IVb (referred to together as "dioxaborolanyl derivative IV" for short hereinbelow) is generally sufficient for further processing. If appropriate, the crude products may be purified further by washing with a solvent which removes the impurities, such as water, or by column chromatography on silica gel with a mixture of methylene chloride and hexane or pentane or with toluene as an eluent.

The yield in step a) is typically from 80 to 100%.

Step b)—Process A1-Hexarylene:

The dioxaborolanyl derivative IV obtained in step a) is subjected in step b) to a Suzuki coupling reaction with a reactant III. In this reaction, either the 9-(dioxaborolan-2-yl)-perylene-3,4-dicarboximide IVa obtained in step a1) is reacted with a naphthalene derivative IIIb (step b1)) or the 1-(dioxaborolan-2-yl)-5-nitronaphthalene IVb obtained in step a2) is reacted with a 9-bromoperylene-3,4-dicarboximide IIIa (step b2)).

The reaction of the dioxaborolanyl derivative IV with the reactant III is carried out in the presence of an organic solvent, if desired in a mixture with water, and also of a transition metal catalyst and of a base.

The molar ratio of 9-(dioxaborolan-2-yl)perylene-3,4-dicarboximide IVa to naphthalene derivate IIIb is generally from 0.8:1 to 3:1, preferably from 0.9:1 to 2:1. The molar ratio of 1-(dioxaborolan-2-yl)-5-nitronaphthalene IVb to 9-bromoperylene-3,4-dicarboximide IIIa is generally from 0.8:1 to 3:1, preferably from 1.5:1 to 2.5:1.

Suitable solvents for step b) are all solvents in which the dioxaborolanyl derivatives IV and the reactants III dissolve fully at reaction temperature and the catalysts and bases used at least partially, so that the reaction conditions are substantially homogeneous. Especially suitable solvents are those already mentioned for step a), preference being given here too to the alkyl-substituted benzenes. The amount of solvent is typically from 10 to 1000 ml, preferably from 20 to 100 ml, per g of dioxaborolanyl derivative IV.

In step b), preference is given to using water as an additional solvent. In this case, generally from 10 to 1000 ml, in particular from 250 to 500 ml, of water are used per l of organic solvent.

The transition metal catalysts used in step b) are likewise preferably palladium complexes, the same preferences applying here as in step a). The use amount of catalyst is typically from 1 to 20 mol %, in particular from 1.5 to 5 mol %, based on the dioxaborolanyl derivative IV.

In step b), as in step a), preferred bases are the alkali metal salts of weak acids, particular preference being given to the carbonates such as sodium carbonate and in particular potassium carbonate. In general, the amount of base is from 0.1 to 10 mol, in particular from 0.2 to 5 mol, per mole of dioxaborolanyl derivative IV.

The reaction temperature is generally from 20 to 180° C., preferably 60 to 120° C. When water is used in step b), it is recommended not to undertake the reaction at temperatures above 100° C., since it would otherwise be necessary to work under pressure.

The reaction is complete typically within from 0.5 to 48 h, in particular within from 5 to 20 h.

In terms of process technology, the procedure in step b) is appropriately as follows: dioxaborolanyl derivative IV and reactant III and also solvent are initially charged, transition metal catalyst and the base, preferably dissolved in water or a water/alcohol mixture, are added, and the mixture is heated to the desired reaction temperature under protective gas for from 0.5 to 48 h. After cooling to room temperature, the organic phase is removed from the reaction mixture and the solvent is distilled off under reduced pressure.

The purity of the thus prepared 9-(5-nitronaphthyl)perylene-3,4-dicarboximide V is generally sufficient for further processing. If appropriate, the crude product may be purified further by washing with water and, if desired, a suitable organic solvent, especially a chlorinated aliphatic or aromatic hydrocarbon, or by column chromatography on silica gel with a mixture of methylene chloride and hexane or pentane or with toluene as an eluent.

The yield in step b) is typically from 90 to 95%.

Step c)—Process A1-Hexarylene:

The 9-(5-nitronaphthyl)perylene-3,4-dicarboximide V obtained in step b) is then converted in step c) by cyclodehydrogenation to the 11-nitroterrylene-3,4-dicarboximide VIa.

The cyclodehydrogenation to the terrylene-3,4-dicarboximide VIa is undertaken in the presence of a base-stable, high-boiling organic solvent and of an alkali metal- or alkaline earth metal-containing base and of a nitrogen-containing auxiliary base.

Suitable solvents are in principle the nonpolar-aprotic and polar-aprotic solvents mentioned for step a).

Preferred nonpolar-aprotic solvents are xylene (all isomers), mesitylene and in particular toluene and decalin; preferred polar-aprotic solvents are diphenyl ether and the dialkyl ether of monomeric and oligomeric ethylene glycol, in particular diethylene glycol dimethyl and diethyl ether.

A particularly preferred solvent is diethylene glycol dimethyl ether.

In addition to the aprotic organic solvents, it is also possible to use protic solvents which comprise amino and hydroxyl functions. Suitable examples here are alcoholamines, especially mono-, di- and tri-$C_2$-$C_4$-alcoholamines, such as mono-, di- and triethanolamine, particular preference being given to ethanolamine.

The amount of solvent is generally from 50 to 250 ml of nonpolar-aprotic solvent, from 10 to 50 ml of polar-aprotic solvent or from 3 to 50 ml of protic solvent, per g of 9-(5-nitronaphthyl)perylene-3,4-dicarboximide V.

Suitable bases are strong organic and inorganic, alkali metal- or alkaline earth metal-containing bases, the alkali metal-containing bases being particularly suitable. Preferred inorganic bases are alkali metal and alkaline earth metal hydroxides and amides; preferred organic bases are alkali metal and alkaline earth metal alkoxides (especially the $C_1$-$C_{10}$-alkoxides, in particular tert-$C_4$-$C_6$-alkoxides), alkali metal and alkaline earth metal (phenyl)alkylamides (especially the bis($C_1$-$C_4$-alkyl)amides) and triphenylmethylmetalates. Particular preference is given to the alkali metal alkoxides. Preferred alkali metals are lithium, sodium and potassium, very particular preference being given to potassium. Particularly suitable alkaline earth metals are magnesium and calcium. It will be appreciated that it is also possible to use mixtures of different bases.

Specific examples of particularly preferred bases include: lithium hydroxide, sodium hydroxide and potassium hydroxide; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide, potassium tert-butoxide, lithium (1,1-dimethyl)octoxide, sodium (1,1-dimethyl)octoxide and potassium (1,1-dimethyl)octoxide; lithium dimethylamide, lithium diethylamide, lithium diisopropylamide, sodium diisopropylamide, triphenylmethyllithium, triphenylmethylsodium and triphenylmethylpotassium.

Very particularly preferred bases are lithium diisopropylamide, sodium methoxide, sodium tert-butoxide, in particular potassium methoxide and potassium hydroxide and especially sodium tert-butoxide and potassium tert-butoxide.

Especially in the case of the use of the alkoxides and of the hydroxides, the reactivity is increased by adding a nitrogen-containing auxiliary base with low nucleophilic action. Suitable bases are the alkylamines which are liquid at the reaction temperatures, especially tri($C_3$-$C_6$-alkyl)amines, such as tripropylamine and tributylamine, alcoholamines, especially mono-, di- and tri($C_2$-$C_4$-alcohol)amines, such as mono-, di- and triethanolamine, and especially heterocyclic bases such as pyridine, N-methylpiperidine, N-methylpiperidone, N-methylmorpholine, N-methyl-2-pyrrolidone, pyrimidine, quinoline, isoquinoline, quinaldine and in particular diazabicyclononene (DBN) and diazabicycloundecene (DBU). It will be appreciated that it is also possible to use mixtures of these auxiliary bases.

Suitable use amounts for the auxiliary base are generally from 1 to 60 g, preferably from 5 to 30 g, per g of 9-(5-nitronaphthyl)perylene-3,4-dicarboximide V. From 2 to 20 mol, preferably from 8 to 20 mol, of the alkali metal base are used per mole of 9-(5-nitronaphthyl)perylene-3,4-dicarboximide V.

The alkali metal base may be used in solid or dissolved form. When the alkali metal base is used in combination with a nonpolar-aprotic reaction solvent in which it is not sufficiently soluble, it can be dissolved in an alcohol which has a higher base strength than the alkali metal base. Suitable alcohols are in particular tertiary aliphatic alcohols which may comprise aryl substituents and have a total of from four to twelve carbon atoms, e.g. tert-butanol, 2-methyl-2-butanol (tert-amyl alcohol), 3-methyl-3-pentanol, 3-ethyl-3-pentanol, 2-phenyl-2-pentanol, 2,3-dimethyl-3-pentanol, 2,4,4-trimethyl-2-pentanol and 2,2,3,4,4-pentamethyl-3-pentanol.

The reaction temperature is typically from 50 to 210° C., preferably from 20 to 100° C.

The reaction time is generally from 0.5 to 24 h, in particular from 0.5 to 4 h.

In process technology terms, the procedure is appropriately to initially charge 9-(5-nitronaphthyl)perylene-3,4-dicarboximide V and base, to add solvent and auxiliary base under protective gas, to heat the mixture to the desired reaction temperature with stirring and under protective gas for the desired time and, after cooling to room temperature, to precipitate the 11-nitroterrylene-3,4:11,12-tetracarboximides VIa formed by diluting with a protic solvent which dissolves the other components, for example with $C_1$-$C_3$-alcohols and in particular water, to filter them off, to wash them with one of the solvents mentioned, especially with one of the alcohols, and subsequently to dry them under reduced pressure.

Occasionally, it may be appropriate to subject the reaction product to an oxidation. This can be done in the simplest manner by blowing atmospheric oxygen into the still-warm reaction mixture. However, it is also possible to add oxidants, preferably hydrogen peroxide, but also aldehyde-containing sugars, e.g. glucose, especially after the reaction.

The purity of the thus prepared 11-nitroterrylene-3,4-dicarboximide VIa is generally sufficient for further processing. If appropriate, the crude product may be recrystallized from a mixture of halogenated solvents, such as chloroform and methylene chloride, and alcohols, such as methanol, ethanol and isopropanol, or from a carboximide such as N-methylpyrrolidone. Alternatively, column chromatography can also be undertaken on silica gel using methylene chloride or hexane or pentane or with toluene as an eluent.

The yield in step c) is typically from 25 to 75%.

Step d)—Process A1-Hexarylene:

The 11-nitroterrylene-3,4-dicarboximide VIa obtained in step c) is reduced in step d) to the corresponding 11-aminoterrylene-3,4-dicarboximide VIb with nascent hydrogen.

The reduction is preferably effected in an acidic, alcoholic-aqueous medium with a metallic reducing agent.

Examples of suitable metallic reducing agents are base metals which are used in very finely divided form, such as iron powder and tin, and also salts of metals in a low oxidation state, such as tin(II) chloride. A preferred reducing agent is iron.

The reduction is effected in the presence of acids, especially inorganic acids, in particular of hydrochloric acid.

In general, from 0.2 to 1.5 g, in particular from 0.8 to 1.5 g, of metallic reducing agent and from 40 to 80 ml, in particular from 20 to 40 ml, of concentrated inorganic acid are used per g of 11-nitroterrylene-3,4-dicarboximide VIa.

Suitable alcoholic solvents are, for example, $C_1$-$C_4$-alcohols such as methanol, ethanol, propanol, isopropanol and butanol, preference being given to ethanol.

Typically, from 100 to 500 ml, in particular from 100 to 200 ml, of alcohol are used per g of 11-nitroterrylene-3,4-dicarboximide VIa.

The reaction temperature is generally from 25 to 90° C., preferably from 75 to 85° C.

The reaction time is typically from 0.5 to 24 h, preferably from 1 to 10 h.

In process technology terms, the procedure in step d) is appropriately to stir a mixture of 11-nitroterrylene-3,4-dicarboximide VIa, metal, acid and alcohol at the desired temperature for from 0.5 to 24 h, then to cool to room temperature and to remove the undissolved metal by filtration from the dissolved 11-aminoterrylene-3,4-dicarboximide VIb, and to wash it repeatedly with a halogenated aliphatic hydrocarbon, e.g. methylene chloride. Subsequently, the organic phase is removed from the filtrate and the solvent is distilled off.

The purity of the thus prepared 11-aminoterrylene-3,4-dicarboximide VIb is typically sufficient for further processing.

The yield in step d) is generally from 75 to 95%.

Instead of the preferred reaction with metal/acid, the 11-nitroterrylene-3,4-dicarboximide VIa may also be hydrogenated catalytically over palladium/activated carbon.

This hydrogenation is preferably undertaken in polar protic reaction medium, especially in a mixture of a halogenated aliphatic hydrocarbon and an alcohol, for example a 2:1 mixture of chloroform and ethanol.

In general, from 10 to 150 ml, in particular from 20 to 80 ml, of reaction medium are used per g of 11-nitroterrylene-3,4-dicarboximide VIa.

The amount of catalyst is typically from 2 to 20 g, preferably from 2 to 5 g, per g of 11-nitroterrylene-3,4-dicarboximide VIa.

The catalytic hydrogenation is typically undertaken at room temperature and lasts generally from 2 to 24 h, in particular from 10 to 16 h.

The 11-aminoterrylene-3,4-dicarboximide VIb prepared can be isolated as described above.

Step e)—Process A1-Hexarylene:

The 11-aminoterrylene-3,4-dicarboximide VIb obtained in step d) is converted in step e) to the corresponding 11-iodo- or 11-bromoterrylene-3,4-dicarboximide VIc.

To this end, the 11-aminoterrylene-3,4-dicarboximide VIb is converted first to a diazonium salt which is then reacted with a metal iodide or bromide.

The diazotization is carried out in a customary manner with a combination of alkali metal nitrite, especially sodium nitrite, an aqueous mineral acid, in particular hydrochloric acid, in the presence of a polar-aprotic organic solvent.

In general, from 1 to 20 g, preferably from 5 to 10 g, of alkali metal nitrite and from 10 to 100 ml, preferably from 30 to 60 ml, of hydrochloric acid are used per g of 11-aminoterrylene-3,4-dicarboximide VIb Suitable polar-aprotic solvents are in particular the protic ethers mentioned in step a), diethyl ether and tetrahydrofuran being particularly suitable, and nitriles such as acetonitrile and propionitrile, particular preference being given to acetonitrile. Preference is given to using mixtures of these solvents.

In general, from 10 to 80 ml, in particular from 20 to 40 ml, of organic solvent are used per g of 11-aminoterrylene-3,4-dicarboximide VIb.

The diazotization is undertaken generally at from −20 to 0° C., in particular at from −10 to −5° C.

The diazonium group is subsequently substituted in the reaction mixture obtained by reaction with a metal iodide or bromide which is soluble in the reaction medium.

Suitable metal halides are in particular the alkali metal halides, preferably the sodium and potassium halides, preference being given to sodium iodide and potassium iodide.

In general, from 1 to 100 g, in particular from 5 to 30 g, of metal halide are used per g of diazonium salt.

The substitution is undertaken typically at from −10 to 20° C., preferably at from −5 to 5° C.

In process technology terms, the procedure in step e) is appropriately as follows:

A solution of 11-aminoterrylene-3,4-dicarboximide VIb in the organic solvent is initially charged and the inorganic acid is slowly added dropwise, followed by, with cooling, a solution of the nitrite in aqueous-organic medium, especially a mixture of water and acetonitrile, at such a slow rate that the temperature does not rise above −5° C. After a continued stirring time of from about 0.25 to 0.5 h at this temperature, the reaction solution is added to a cooled mixture of metal halide and aqueous-organic medium, especially water and acetonitrile, and stirred at about 0° C. for from about 0.5 to 2 h, and the mixture is then allowed to warm slowly to room temperature. The reaction product is isolated by extraction with a halogenated aliphatic hydrocarbon, for example methylene chloride, the extract is washed with water and the solvent is distilled off.

For purification, the resulting 11-haloterrylene-3,4-dicarboximide VIc is washed with the aqueous solution of a reducing agent, preferably with a sodium sulfite solution, and finally with water, and subsequently dried under reduced pressure. If desired, column chromatography may additionally be undertaken on silica gel with a mixture of methylene chloride and hexane or pentane or with toluene as an eluent. In general, the 11-haloterrylene-3,4-dicarboximide VIc can, however, also be used without purification for the subsequent step f).

The yield in step e) is generally from 20 to 25%.

Step f)—Process A1-Hexarylene:

The 11-haloterrylene-3,4-dicarboximide VIc obtained in step e) is coupled in step f) to give the bisterrylene derivative VII.

The coupling can be effected f1) in the presence of an organic transition metal complex as a catalyst, of free ligand molecules and of an aprotic solvent in a homo-coupling, or f2) in the presence of from 30 to 70 mol %, based on the 11-haloterrylene-3,4-dicarboximide VIc, of a diborane II, of a transition metal catalyst, of a base and of an aprotic solvent in a Suzuki coupling reaction, in which case the 11-(dioxaborolan-2-yl)-terrylene-3,4-dicarboximide VId formed in situ is not intermediately isolated, but rather reacted directly with the remaining 11-haloterrylene-3,4-dicarboximide VIc.

It will be appreciated that the 11-(dioxaborolan-2-yl)terrylene-3,4-dicarboximide VId can also be prepared and intermediately isolated separately from the 11-haloterrylene-3,4-dicarboximide VIc and subsequently coupled in a further reaction step with 11-haloterrylene-3,4-dicarboximide VIc. This procedure is the subject matter of the process A2-hexarylene and is especially suitable for preparing hexarylenetetracarboximides Ia which are unsymmetrically substituted (different R radicals on the two imide nitrogen atoms and/or different R' radicals in the two terrylene units).

Inert diluents especially suitable for the process variant f1) are, for example, aliphatic carboxamides such as N,N-dimethylformamide and N,N-dimethylacetamide, aliphatic and cycloaliphatic ethers such as 1,2-dimethoxyethane and tetrahydrofuran, and aromatics such as benzene, toluene and xylene, preference being given to N,N-di-methylformamide and N,N-dimethylacetamide.

The amount of diluent is generally from 20 to 100 g, preferably from 25 to 45 g, per g of 11-haloterrylene-3,4-dicarboximide VIc.

Useful organic transition metal complexes which serve as a catalyst are not only the palladium complexes already mentioned for step a), of which preference is given to tetrakis(triphenylphosphine)palladium(0), but also especially nickel complexes, for example bis(triphenylphosphine)nickel(II) chloride, tetrakis(triphenylphosphine)-nickel(0), [1,2-bis(diphenylphosphino)ethane]nickel(II) chloride and preferably bis(1,5-cyclooctadiene)nickel(0).

It is also possible to obtain the catalysts in situ by adding transition metal salts or compounds, free ligands such as cyclooctadiene, bipyridyl, triphenylphosphine, trifluorophosphine, η-, δ- and π-bonded olefins, cycloolefins, aromatics and antiaromatics, carbonyls, hydrogen and halogen and also mixtures thereof, and if required oxidizing or reducing agents.

In general, from 40 to 150 mol %, preferably from 50 to 100 mol %, of organic transition metal complex, based on the 11-haloterrylene-3,4-dicarboximide VIc, is used.

In general, the simultaneous presence of free ligand molecules is always recommended, especially mixtures of cyclooctadiene and bipyridyl in a molar ratio of from 1:1 to 8:1. Suitable amounts are typically from 80 to 900 mol %, preferably from 80 to 200 mol %, based on the 11-haloterrylene-3,4-dicarboximide VIc.

The coupling temperature is generally from 40 to 80° C., preferably from 60 to 70° C.

The reaction time is generally from 24 to 48 h, in particular from 36 to 48 h.

In process technology terms, the procedure in step f1) is appropriately to initially charge 11-haloterrylene-3,4-dicarboximide VIc, organometallic catalyst and free ligand molecules in the inert diluent, and, if appropriate under protective gas, to heat them to the desired reaction temperature for from 24 to 48 h. After cooling, the reaction mixture is introduced into water which may comprise methanol if appropriate, dilute inorganic acid, for example dilute hydrochloric acid, is added and the precipitate formed is filtered off, washed with water and dried under reduced pressure.

The purity of the thus prepared bisterrylene derivative VII is generally sufficient for the subsequent cyclodehydrogenation. If appropriate, the product may additionally be further purified by column chromatography on silica gel with a mixture of methylene chloride and hexane or pentane as an eluent.

The yield in step f1) is generally from 70 to 90%.

In process variant f2), the procedure is analogous to step a) and b), except that only from 30 to 70 mol % of diborane II, based on the 11-haloterrylene-3,4-dicarboximide VIc, are used for the in situ formation of the 11-(dioxaborolan-2-yl)terrylene-3,4-dicarboximide VId.

In general, from 1 to 20 mol %, preferably from 5 to 10 mol %, of transition metal catalyst, and from 1 to 5 mol, preferably from 2 to 3 mol, of base are used per mole of 11-haloterrylene-3,4-dicarboximide VIc. The aprotic organic solvent is used typically in amounts of from 10 to 100 ml, in particular from 20 to 50 ml, per g of 11-haloterrylene-3,4-dicarboximide VIc.

The reaction temperature is generally from 20 to 100° C., preferably from 60 to 80° C., and the reaction time from 12 to 72 h, preferably from 24 to 48 h.

In process technology terms, the procedure in step f2) is appropriately as follows:

11-haloterrylene-3,4-dicarboximide VIc and solvent are initially charged, the diborane II, the transition metal catalyst and the base are added successively and the mixture is heated to the desired reaction temperature for from 12 to 72 h. After cooling to room temperature, the organic phase is removed from the reaction system and the solvent is distilled off under reduced pressure.

Here too, the purity of the resulting bisterrylene derivative VII is generally sufficient for the subsequent cyclodehydrogenation. As in step f1), a further purification by column chromatography is, however, possible.

The yield in step f2) is typically from 80 to 95%.

Step g)—Process A1-Hexarylene:

The bisterrylene derivative VII obtained in step f) is cyclodehydrogenated in step g) to the hexarylenetetracarboximide Ia.

The cyclodehydrogenation may be undertaken g1) in an organic reaction medium which has hydroxyl and amino functions and comprises a substantially undissolved base or g2) as in step c), in the presence of a base-stable, high-boiling organic solvent and of an alkali metal- or alkaline earth metal-containing base and of a nitrogen-containing auxiliary base.

Preference is given to the process variant g1) which is described in detail hereinbelow.

Suitable organic reaction media are in particular amino alcohols which have from 2 to 20, preferably from 2 to 10, carbon atoms. The carbon chain of these alcohols may be interrupted by oxygen atoms in ether function. Examples of particularly suitable solvents are ethanolamine, triethanolamine and diethanolamine, preference being given to ethanolamine. It is also possible to use mixtures of alcohols and amines, each of which has a boiling point of at least 70° C. and is liquid at the reaction temperature.

Typically, from 1.5 to 150 ml, preferably from 5 to 50 ml, of reaction medium are used per g of bisterrylene derivative VII.

Suitable bases which are substantially insoluble in the reaction medium are the alkali metal salts, especially the sodium salts and in particular the potassium salts, weak organic and preferably weak inorganic acids, such as formates, acetates, propionates, hydrogencarbonates and more preferably carbonates, especially sodium carbonate and in particular potassium carbonate.

In general, the amount of base is from 1 to 10 mol, preferably from 2 to 5 mol, per mole of bisterrylene derivative VII.

The reaction temperature is generally from 40 to 200° C., in particular from 80 to 160° C.

The reaction time is typically from 0.5 to 24 h, preferably from 1 to 12 h.

In process technology terms, the procedure in step g) is appropriately to stir a mixture of bisterrylene derivative VII, solvent and base at the desired reaction temperature under protective gas for from 0.5 to 24 h and, after cooling to room temperature, to precipitate the hexarylenetetracarboximide Ia formed out of the reaction mixture by addition of an alcohol such as ethanol or of water, to filter it off and to wash it with water.

The purification of the resulting hexarylenetetracarboximide Ia may be undertaken as follows: catalyst residues may be removed by rapid filtration through silica gel with washing with a halogenated aliphatic hydrocarbon such as methylene chloride. Residues of unconverted reactants based on perylene and terrylene may be removed by column chromatography on silica gel with methylene chloride as an eluent or by repeated washing with hexane or pentane.

The yield in step g1) is generally from 90 to 100%.

In process variant g2), the procedure is analogous to step c).

The resulting hexarylenetetracarboximide Ia can be isolated and purified as in step g1).

The yield in step g2) is typically from 90 to 95%.

Process A2-Hexarylene:

Step a)—Process A2-Hexarylene:

In the inventive process A2 for preparing hexarylenetetracarboximides Ia which are (het)aryloxy- and (het)arylthio-substituted in the rylene ring, a diborane II is reacted in step a) with an 11-haloterrylene-3,4-dicarboximide VIc, which should be prepared as described in process A1-hexarylene, analogously to step a) of process A1-hexarylene, in the presence of an aprotic organic solvent, of a transition metal catalyst and of a base.

In process technology terms, the procedure is appropriately likewise as described for step a) of process A1-hexarylene. A further purification of the 11-(dioxaborolan-2-yl)terrylene-3,4-dicarboximide VId which is isolated here too by filtering off the solid constituents and distilling off the solvent is typically again not required, but may likewise be effected by column chromatography on silica gel with a mixture of methylene chloride and hexane or pentane or with toluene as an eluent.

The yield in step a) is typically from 80 to 100%.

Step b)—Process A2-Hexarylene:

The 11-(dioxaborolan-2-yl)terrylene-3,4-dicarboximide VId obtained in step a) is subjected in step b) to a Suzuki coupling reaction with an 11-haloterrylene-3,4-dicarboximide VIc.

In this reaction, it is possible to use an 11-haloterrylene-3,4-dicarboximide VIc which is either identical to the 11-haloterrylene-3,4-dicarboximide VIc used for the preparation of the 11-(dioxaborolan-2-yl)terrylene-3,4-dicarboximide VId or is different therefrom (bears other R and/or R' radicals). In the first case, symmetrical hexarylenetetra-carboximides are obtained, while unsymmetrical hexarylenetetracarboximides can be obtained in the second case.

As described in step b) of process A1-hexarylene, the reaction is carried out in the presence of an organic solvent, if desired in a mixture with water, and also of a transition metal catalyst and of a base.

In process technology terms, the procedure is appropriately likewise as described for step b) of process A1-hexarylene. A further purification of the bisterrylene derivative VII which is isolated here too by removing the organic phase and distilling off the solvent is typically again not required but can likewise be effected by washing with a solvent which dissolves the impurities, such as water, or by column chromatography on silica gel with a mixture of methylene chloride and hexane or pentane or with toluene as an eluent.

The yield in step b) is typically from 80 to 95%.

Step c)—Process A2-Hexarylene:

The cyclodehydrogenation of the bisterrylene derivative VII obtained in step b) to the hexarylenetetracarboximide Ia in step c) corresponds to step g) of process A1-hexarylene. Here too, preference is given to the procedure c1) analogous to step g1) of process A1-hexarylene.

This process too makes it possible to obtain either symmetrical or unsymmetrical hexarylenetetracarboximides Ia (different R radicals on the two imide nitrogen atoms and/or different R' radicals in the two terrylene units).

Process A1-Pentarylene:

In analogy to process A1-hexarylene, in the inventive process A1 for preparing pentarylenetetracarboximides Ib which are (het)aryloxy- and (het)arylthio-substituted in the rylene ring, an 11-haloterrylene-3,4-dicarboximide VIc and a 9-(dioxaborolan-2-yl)perylene-3,4-dicarboximide IVa are subjected to a Suzuki coupling reaction and the 11-(9-perylene-3,4-dicarboximide)terrylene-3,4-dicarboximide VIII formed is cylclodehydrogenated.

Step a)—Process A1-Pentarylene:

The Suzuki coupling reaction between the 11-haloterrylene-3,4-dicarboximide VIc, which should be prepared as described in process A1-hexarylene, and the 9-(dioxaborolan-2-yl)perylene-3,4-dicarboximide IVa in step a) is undertaken analogously to step b) of process A1-hexarylene in the presence of an organic solvent, if desired in a mixture with water, and also of a transition metal catalyst and of a base.

In process technology terms, the procedure is likewise analogous to step b) of process A1-hexarylene. A further purification of the 11-(9-perylene-3,4-dicarboximide)-terrylene-3,4-dicarboximide VIII which has been isolated by removing the organic phase and distilling off the solvent is typically again not required, but may likewise be effected by washing with a solvent which dissolves the impurities, such as water, or by column chromatography on silica gel with a mixture of methylene chloride and hexane or pentane or with toluene as an eluent.

The yield in step a) is typically from 90 to 95%.

Step b)—Process A1-Pentarylene:

The cyclodehydrogenation of the 11-(9-perylene-3,4-dicarboximide)terrylene-3,4-dicarboximide VIII to the pentarylenetetracarboximide Ib may be undertaken b1) analogously to step g1) of process A1-hexarylene in an organic reaction medium having hydroxyl and amino functions and comprising a substantially undissolved base or b2) analogously to step g2) of process A1-hexarylene in the presence of a base-stable, high-boiling organic solvent and of an alkali metal- or alkaline earth metal-containing base. Here too, preference is given to process variant b1) (and thus also to process variant a1)).

In process technology terms, the procedure is likewise appropriately analogous to step g1) or g2) of process A1-hexarylene.

To purify the resulting pentarylenetetracarboximide Ib, it is likewise possible to undertake a rapid filtration through silica gel with washing with a mixture of polar- and nonpolar-aprotic solvents, for example methylene chloride/hexane or pentane, and also column chromatography on silica gel with methylene chloride as an eluent or repeated washing with hexane or pentane.

The yield in step b1) is generally from 90 to 100%; the yield in step b2) is typically from 90 to 100%.

With the aid of the inventive process A1-pentarylene, both symmetrical and unsymmetrical pentarylenetetracarboximides Ia (different R radicals on the two imide nitrogen atoms and/or different R' radicals in the terrylene and in the perylene unit) are obtainable.

Process A2-Pentarylene:

In analogy to process A2-hexarylene, in the inventive process A2 for preparing pentarylenetetracarboximides Ib which are (het)aryloxy- and (het)arylthio-substituted in the rylene ring, an 11-(dioxaborolan-2-yl)terrylene-3,4-dicarboximide VId and a 9-bromoperylene-3,4-dicarboximide IIa are subjected to a Suzuki coupling reaction, and the 11-(9-perylene-3,4-dicarboximide)terrylene-3,4-dicarboximide VIII formed is cyclodehydrogenated.

Step a)—Process A2-Pentarylene:

The Suzuki coupling reaction between the 11-(dioxaborolan-2-yl)terrylene-3,4-dicarboximide VId, which should be prepared as described in step a) of process A2-hexarylene, and the 9-bromoperylene-3,4-dicarboximide IIIa in step a) is undertaken analogously to step b) of process A1-hexarylene in the presence of an organic solvent, if desired in a mixture with water, and also of a transition metal catalyst and of a base.

In process technology terms, the procedure is appropriately likewise analogous to step b) of process A1-hexarylene. A further purification of the 11-(9-perylene-3,4-dicarboximide)terrylene-3,4-dicarboximide VIII which has been isolated by removing the organic phase and distilling off the solvent is typically again not required, but may likewise be effected by washing with a solvent which dissolves the impurities, such as water, or by column chromatography on silica gel with a mixture of methylene chloride and hexane or pentane or with toluene as an eluent.

The yield in step a) is typically from 90 to 95%.

Step b)—Process A2-Pentarylene:

The cyclodehydrogenation of the 11-(9-perylene-3,4-dicarboximide)terrylene-3,4-dicarboximide VIII obtained in step a) to the pentarylenetetracarboximide Ib corresponds to step b) of process A1-pentarylene.

With the aid of the inventive process A2-pentarylene, it is possible to obtain both symmetrical and unsymmetrical pentarylenetetracarboximides Ia (different R radicals on the two imide nitrogen atoms and/or different R' radicals in the terrylene and in the perylene unit).

Process B-Hexarylene:

The inventive process B-hexarylene allows hexarylenetetracarboximides Ia which are either (het)aryloxy- and (het)arylthio-substituted in the rylene ring or unsubstituted in the rylene ring to be obtained.

Step a)—Process B-Hexarylene:

In step a) of this process, a diborane II is reacted with a1) a 9-bromoperylene-3,4-dicarboximide IIIa or a2) a 3,9- or 3,10-dihaloperylene IXa.

The dihaloperylenes IXa are typically mixtures of the 3,9- and 3,10-isomer. Accordingly, the bis(dioxaborolan-2-yl)perylenes IXb prepared from them in step a) are also obtained as a mixture of 3,9- and 3,10-isomer. This applies correspondingly to the coupling products Xa and Xb formed in step b) from the disubstituted perylenes IXa or IXb. For the sake of simplicity, the particular isomers are listed in the description and the claims as separate species. However, the invention is also intended to comprise the isomer mixtures.

The reaction is undertaken analogously to step a) of process A1-hexarylene in the presence of an aprotic organic solvent, of a transition metal catalyst and of a base.

Since both halogen atoms of the dihaloperylene IXa are replaced by dioxaborolan-2-yl radicals, double the amount of diborane II is required here, i.e. typically from 2 to 4 mol, in particular from 2 to 3 mol, of diborane II are used per mole of dihaloperylene IXa.

The amount of transition metal catalyst and base should likewise be doubled; the amount of solvent and the further reaction conditions correspond to step a) of process A1-hexarylene.

In process technology terms, the procedure is appropriately likewise as described for step a) of process A1-hexarylene. A further purification of the 9-(dioxaborolan-2-yl)perylene-3,4-dicarboximide IVa and/or 3,9- or 3,10-bis(dioxaborolan-2-yl)perylene IXb which is isolated here too by filtering off the solid constituents and distilling off the solvent is typically again not required, but may likewise be effected by washing with a solvent which dissolves the impurities, such as water, or by column chromatography on silica gel with a mixture of methylene chloride and hexane or pentane or with toluene as an eluent.

The yield in step a) is typically from 75 to 95%.

Step b)—Process B-Hexarylene:

The dioxaborolanyl derivative obtained in step a) is subjected in step b) to a double Suzuki coupling reaction with a halogenated perylene reactant. In this reaction either the 9-(dioxaborolan-2-yl)perylene-3,4-dicarboximide IVa obtained in step a1) is reacted with a 3,9- or 3,10-dihaloperylene IXa (step b1)) or the 3,9- and/or 3,10-bis(dioxaborolan-2-yl)perylene IXb obtained in step a2) is reacted with a 9-bromoperylenedicarboximide IIIa (step b2)).

The perylene derivatives IXa or IXb capable of carrying out two coupling reactions form the middle sections and the perylene-3,4-dicarboximides IVa or IIIa the end sections of the resulting coupling product.

The molar ratio of 9-(dioxaborolan-2-yl)perylene-3,4-dicarboximide IVa to dihaloperylene IXa or of 9-bromoperylenedicarboximide IIa to bis(dioxaborolan-2-yl)perylene IXb is accordingly typically from 2:1 to 4:1, preferably from 2:1 to 3:1.

By virtue of use of two different 9-(dioxaborolan-2-yl)perylene-3,4-dicarboximides IVa or 9-bromoperylenedicarboximides IIIa, the possibility exists here too of preparing unsymmetrical hexarylenetetracarboximides Ia.

The coupling is carried out analogously to step b) of process A1-hexarylene in the presence of an organic solvent, if desired in a mixture with water, and also of a transition metal catalyst and of a base.

However, double the amounts again of transition metal catalyst and base are used. The amount of solvent and the further reaction conditions correspond to step b) of process A1-hexarylene.

In process technology terms, the procedure is appropriately likewise as described for step b) of process A1-hexarylene. A further purification of the perylene-3,9-bis(perylene-3,4-dicarboximide) Xa and/or perylene-3,10-bis(perylene-3,4-dicarboximide) Xb which is isolated here too by removing the organic phase and distilling off the solvent is typically again not required, but may likewise be effected by washing with a solvent which dissolves the impurities, such as water, or by column chromatography on silica gel with a mixture of methylene chloride and hexane or pentane or with toluene as an eluent.

The yield in step b) is typically from 70 to 90%.

Step c)—Process B-Hexarylene:

The cyclodehydrogenation of the perylene-3,9-bis(perylene-3,4-dicarboximide) Xa and/or perylene-3,10-bis(perylene-3,4-dicarboximide) Xb obtained in step b) to the hexarylenetetracarboximide Ia may be undertaken either in one stage (variant c1) or in two stages (variant c2).

In the one-stage procedure c1), the perylene-3,9-bis(perylene-3,4-dicarboximide) Xa and/or perylene-3,10-bis(perylene-3,4-dicarboximide) Xb is contacted with a strong Lewis acid in the presence of an inert organic solvent.

Suitable solvents are in principle all organic solvents which are inert under the reaction conditions, preference being given to polar-aprotic solvents.

Examples of particularly suitable solvents are halogenated and nitrated aromatic hydrocarbons such as chlorobenzene, di- and trichlorobenzenes and nitrobenzene.

The amount of solvent is generally from 10 to 100 ml, preferably from 20 to 40 ml, per g of perylene-3,9-bis(perylene-3,4-dicarboximide) Xa and/or perylene-3,10-bis(perylene-3,4-dicarboximide) Xb.

Suitable strong Lewis acids are in particular aluminum trihalides, such as aluminum trichloride and aluminum tribromide, preference being given to aluminum trichloride.

Typically from 2 to 10 mol, preferably from 6 to 8 mol, of Lewis acid are used per mole of perylene-3,9-bis(perylene-3,4-dicarboximide) Xa and/or perylene-3,10-bis(perylene-3,4-dicarboximide) Xb.

The reaction temperature is generally from 20 to 120° C., preferably from 45 to 80° C.

The reaction time is generally from 0.25 to 48 h, in particular from 0.25 to 8 h.

In process technology terms, the procedure is appropriately to stir a mixture of perylene-3,9-bis(perylene-3,4-dicarboximide) Xa and/or perylene-3,10-bis(perylene-3,4-dicarboximide) Xb, solvent and Lewis acid at the desired reaction temperature for from 0.25 to 28 h, to distill off the solvent after cooling to room temperature and to wash the hexarylenetetracarboximide Ia formed first with dilute inorganic acid, for example dilute hydrochloric acid, and then with water, and to filter it off.

For further purification, the (het)aryloxy- or (het)arylthio-substituted hexarylene-tetracarboximides Ia may be washed repeatedly with hexane or pentane, and subjected to a rapid filtration through silica gel with washing with a halogenated aliphatic hydrocarbon, such as methylene chloride, or column chromatography on silica gel with methylene chloride as an eluent. Unsubstituted hexarylenetetracarboximides Ia (R'=H) may be purified by washing with acetone and subsequently with methylene chloride.

The yield in the one-stage cyclodehydrogenation c1) is generally from 20 to 30%.

In the two-stage procedure c2), the perylene-3,9-bis(perylene-3,4-dicarboximide) Xa and/or perylene-3,10-bis(perylene-3,4-dicarboximide) Xb is contacted in a first step c2a) with a weak Lewis acid at room temperature in the presence of an inert organic solvent.

The 13-(9-perylene-3,4-dicarboximide)quaterrylene-3,4-dicarboximide XI is then, after intermediate isolation, in a second step c2b) analogous to step g) of process A1-hexarylene, cyclodehydrogenated further to the hexarylenetetracarboximide Ia. The cyclodehydrogenation may be undertaken c2bα) in an organic reaction medium which has hydroxyl and amino functions and comprises a substantially undissolved base (analogously to step g1) of process A1-hexarylene) or c2bβ) in the presence of a base-stable, high-boiling organic solvent and also of an alkali metal- or alkaline earth metal-containing base and of a nitrogen-containing auxiliary base (analogously to step g2) of process A1-hexarylene). Here too, preference is given to process variant c2a).

The two-stage procedure c2) has the advantage that, owing to the milder reaction conditions in the first cyclodehydrogenation step c2a), the risk of undesired elimination of alkyl substituents on the aromatic R or R' radicals is reduced.

In step c2a), the same solvents may be used in the same amounts as in the one-stage procedure c1), the same preferences applying.

Suitable weak Lewis acids are in particular iron(III) halides such as iron(III) chloride and iron(III) bromide, preference being given to iron(III) chloride. The weak Lewis acids may be used in the same amounts as the strong Lewis acids in the one-stage procedure c1).

However, the reaction is carried out in step c2a) at temperatures around room temperature, i.e. it is generally unnecessary to heat the reaction mixture.

The reaction times are typically from about 4 to 48 h, in particular from 8 to 24 h.

In process technology terms, the procedure is appropriately to heat perylene-3,9-bis(perylene-3,4-dicarboximide) Xa and/or perylene-3,10-bis(perylene-3,4-dicarboximide) Xb, solvent and Lewis acid to the desired reaction temperature under protective gas for from 4 to 48 h and to isolate the 13-(9-perylene-3,4-dicarboximide)quaterrylene-3,4-dicarboximide XI formed by distilling off the solvent and subsequently washing first with dilute inorganic acid, for example dilute hydrochloric acid, and then with water.

The purity of the thus prepared 13-(9-perylene-3,4-dicarboximide)quaterrylene-3,4-dicarboximide XI is generally sufficient for the second cyclodehydrogenation step c2b). If appropriate, the crude product can be purified further by column chromatography on silica gel with methylene chloride as an eluent.

The yield in step c2a) is generally from 30 to 40%.

The second cyclodehydrogenation step c2b) to the hexarylenetetracarboximide Ia is undertaken analogously to step g1) of process A1-hexarylene, preferably in an organic reaction medium which has hydroxyl and amino functions and comprises a substantially undissolved base (step c2bα)), but may also be carried out analogously to step g2) of process A1-hexarylene in the presence of a base-stable, high-boiling organic solvent and also of an alkali metal- or alkaline earth metal-containing base and of a nitrogen-containing auxiliary base (step c2bβ)).

In process technology terms, the procedure is appropriately likewise as described for step g) of process A1-hexarylene.

The further purification of the resulting hexarylenetetracarboximide Ia may be undertaken as in the one-stage procedure c1).

The yield in step c2bα) is generally from 80 to 100%; the yield in step c2bβ) is typically from 80 to 95%.

With the aid of the inventive process B-hexarylene, it is possible to obtain both symmetrical and unsymmetrical hexarylenetetracarboximides Ia (different R radicals on the two imide nitrogen atoms and/or different R' radicals in the two outer perylene units).

Process B-Pentarylene:

The inventive process B-pentarylene which is analogous to process B-hexarylene makes it possible to obtain pentarylenetetracarboximides Ib which are either (het)aryloxy- and (het)arylthio-substituted in the rylene ring or unsubstituted in the rylene ring to be obtained.

Step a)—Process B-Pentarylene:

In step a) of this process, a diborane II is reacted with a1) a 9-bromoperylene-3,4-dicarboximide IIIa or a2) a 1,5- or 1,4-dihalonaphthalene IXc.

This reaction is undertaken analogously to step a) of process A1-hexarylene in the presence of an aprotic organic solvent, of a transition metal catalyst and of a base.

Since both halogen atoms of the dihalonaphthalene IXc are replaced in step a2) by dioxaborolan-2-yl radicals, double the amount of diborane II is required here, i.e. typically from 2 to 4 mol, in particular from 2 to 3 mol of diborane II are used per mole of dihaloperylene IXc.

Analogously to process B-hexarylene, the amount of transition metal catalyst and base should likewise be doubled; the amount of solvent and the further reaction conditions correspond to step a) of process A1-hexarylene.

In process technology terms, the procedure is appropriately likewise analogous to step a) of process A1-hexarylene. A further purification of the isolated 9-(dioxaborolan-2-yl)perylene-3,4-dicarboximide IVa or 1,5- or 1,4-bis(dioxaborolan-2-yl)naphthalene IXd which has been isolated here too by filtering off the solid constituents and distilling off the solvent is typically again not required here, but may likewise be effected by washing with a solvent which dissolves the impurities, such as water, or by column chromatography on silica gel with a mixture of methylene chloride and hexane or pentane as an eluent.

The yield in step a) is typically from 80 to 95%.

Step b)—Process B-Pentarylene:

The dioxaborolanyl derivative obtained in step a) is subjected in step b) to a double Suzuki coupling reaction with a halogenated naphthalene or perylene reactant. In this reaction, either the 9-(dioxaborolan-2-yl)perylene-3,4-dicarboximide IVa obtained in step a1) is reacted with a 1,5- or 1,4-dihalonaphthalene IXc (step b1)) or the 1,5- or 1,4-bis(dioxaborolan-2-yl)naphthalene IXd obtained in step a2) is reacted with a 9-bromoperylenedicarboximide IIIa (step b2)).

The naphthalene derivatives IXc and IXd capable of carrying out two coupling reactions form the middle sections and the perylene-3,4-dicarboximides IVa and IIIa the end sections of the resulting coupling product.

The molar ratio of 9-(dioxaborolan-2-yl)perylene-3,4-dicarboximide IVa to dihalonaphthalene IXc or of 9-bromoperylenedicarboximide IIIa to bis(dioxaborolan-2-yl)naphthalene IXd is accordingly typically from 2:1 to 4:1, preferably from 2:1 to 3:1.

By virtue of use of two different 9-(dioxaborolan-2-yl)perylene-3,4-dicarboximides IVa or 9-bromoperylenedicarboximides IIIa, the possibility exists here too of preparing unsymmetrical pentarylenetetracarboximides Ia.

The coupling is carried out analogously to step b) of process A1-hexarylene in the presence of an organic solvent, if desired in a mixture with water, and also of a transition metal catalyst and of a base.

However, double amounts of transition metal catalyst and base again are used. The amount of solvent and the further reaction conditions correspond to step b) of process A1-hexarylene.

In process technology terms, the procedure is appropriately likewise analogous to step b) of process A1-hexarylene. A further purification of the naphthalene-1,5-bis(perylene-3,4-dicarboximide) XIIa or naphthalene-1,4-bis(perylene-3,4-dicarboximide) XIIb which has been isolated here too by removing the organic phase and distilling off the solvent is typically again not required, but may likewise be carried out by washing with a solvent which dissolves the impurities, such as water, or by column chromatography on silica gel with a mixture of methylene chloride and hexane or pentane as an eluent.

The yield in step b) is typically from 80 to 90%.

Step c)—Process B-Pentarylene:

The cyclodehydrogenation of the naphthalene-1,5-bis(perylene-3,4-dicarboximide) XIIa or naphthalene-1,4-bis(perylene-3,4-dicarboximide) XIIb obtained in step b) to the pentarylenetetracarboximide Ib may be undertaken analogously to step c) of process B-hexarylene, likewise in one stage (variant c1)) or two stages (variant c2)).

In the one-stage procedure c1), the naphthalene-1,5-bis(perylene-3,4-dicarboximide) XIIa or naphthalene-1,4-bis(perylene-3,4-dicarboximide) XIIb is contacted with a strong Lewis acid analogously to the one-stage procedure in step c) of process B-hexarylene in the presence of an inert organic solvent.

In process technology terms, the procedure is appropriately likewise analogous to step c1) of process B-hexarylene. A purification of the pentarylenetetracarboximide Ib which has been isolated here too by distilling off the solvent may, in the case of the (het)aryloxy- or (het)arylthio-substituted pentarylenetetracarboximides Ib, likewise be effected by repeatedly washing with hexane or pentane, by a rapid filtration through silica gel with washing with a halogenated aliphatic hydrocarbon such as methylene chloride, or column chromatography on silica gel with methylene chloride as the eluent. Unsubstituted pentarylenetetracarboximides Ib (R'=H) may be purified by washing with acetone and subsequently with methylene chloride.

The yield in the case of one-stage cyclodehydrogenation c) is typically from 20 to 35%.

In the two-stage procedure c2), the naphthalene-1,5-bis(perylene-3,4-dicarboximide) XIIa or naphthalene-1,4-bis(perylene-3,4-dicarboximide) XIIb is contacted in a first step c2a) with a weak Lewis acid at room temperature in the presence of an inert organic solvent.

The thus formed 11-(9-perylene-3,4-dicarboximide)terrylene-3,4-dicarboximide VIII is then, after intermediate isolation, cyclodehydrogenated in a second step c2b) further to the pentarylenetetracarboximide Ib. The cyclodehydrogenation may be undertaken c2bα) in an organic reaction medium which has hydroxyl and amino functions and comprises a substantially undissolved base (analogously to step g1) of process A1-hexarylene) or c2bβ) in the presence of a base-stable high-boiling organic solvent and also of an alkali metal- or alkaline earth metal-containing base and of a nitrogen-containing auxiliary base (analogously to step g2) of process A1-hexarylene). Here too, preference is given to process variants c2bα).

As in process B-hexarylene, the two-stage procedure c2) has the advantage that, owing to the milder reaction conditions in the first cyclodehydrogenation step, the risk of undesired elimination of alkyl substituents on the aromatic R or R' radicals is reduced.

The first cyclodehydrogenation (step c2a)) is undertaken analogously to step c2a) of process B-hexarylene.

In process technology terms, the procedure is appropriately likewise analogous to step c2a) of process B-hexarylene.

The yield in step c2a) is generally from 30 to 40%.

The second cyclodehydrogenation step c2b) to the pentarylenetetracarboximide Ib is likewise preferably carried out analogously to step c2b) of process B-hexarylene which is in turn undertaken analogously to step g1) of process A1-hexarylene (step c2bα)). However, it will be appreciated that the process variant c2bβ) analogous to step g1) of process A1-hexarylene may also be selected here.

In process technology terms, the procedure is appropriately likewise analogous.

The resulting pentarylenetetracarboximide Ib may be purified as described for the one-stage process variant c1).

The yield in step c2bα) is generally from 80 to 100%; the yield in c2bβ) is typically from 80 to 95%.

With the aid of the inventive process B-pentarylene, it is possible to obtain both symmetrical and unsymmetrical pentarylenetetracarboximides Ib (different R radicals on the two imide nitrogen atoms and/or different R' radicals in the two outer perylene units).

The inventive rylenetetracarboximides I exhibit strong absorption in the near infrared region at wavelengths of from 830 to 975 nm and thus complement the spectral region accessible with the aid of the rylene compounds known to date in an advantageous manner.

They are suitable for a multitude of applications, such as the coloring of high molecular weight organic and inorganic materials, for example of coatings, printing inks and plastics, for producing aqueous polymer dispersions which absorb in the near infrared region of the electromagnetic spectrum, for producing markings and inscriptions which absorb infrared light and are invisible to the human eye, as infrared absorbers for heat management, as IR laser beam-absorbing materials in fusion treatment of plastics parts, and also as active components in photovoltaics.

EXAMPLES

Example 1

N,N'-bis(2,6-diisopropylphenyl)-1,6,15,20-tetra[4-(1,1,3,3-tetramethylbutyl)-phenoxy]hexarylene-3,4:17,18-tetracarboximide Ia' a) Preparation of 1-(4,4,5,5-tetramethyl-1,3,2-dioxaboran-2-yl)-5-nitronaphthalene IVb'

A solution of 6.0 g (23.8 mmol) of 1-bromo-5-nitronaphthalene in 100 ml of dioxane was purged with argon. 14.0 g (61.6 mmol) of potassium acetate, 12.0 g (47.3 mmol) of bis(pinacolato)diborane and 0.8 g (0.97 mmol) of [1,1'-bis(diphenylphosphino)-ferrocene]palladium(II) chloride were then added. After once again purging with argon, the mixture was heated to 70° C. and stirred at this temperature for 16 h. After cooling to room temperature, the reaction mixture was extracted with methylene chloride. The organic phase was washed twice with water and dried over magnesium sulfate. The solvent was then distilled off under reduced pressure. Subsequently, the crude product was subjected to column chromatography on silica gel with methylene chloride as the eluent.

6.9 g of IVb' were obtained in the form of a pale yellow solid, which corresponds to a yield of 97%.

Analytical Data:

Melting point: 111° C.; Elemental analysis ($C_{16}H_{18}BNO_4$) (% by weight calc./found): C, 64.24/64.43; H, 6.07/6.14; N, 4.68/4.61.

$^1$H NMR (250 MHz, $CD_2Cl_2$, 25° C.): δ=9.14 (dd, 1H, J=8.5 and 1.0 Hz); 8.58 (dd, 1H, J=8.9 and 1.0 Hz); 8.20 (dd, 1H, J=7.0 and 1.3 Hz); 8.15 (dd, 1H, J=7.0 and 1.3 Hz); 7.70 (t, 1H); 7.60 (t, 1H); 1.33 ppm (s, 12H);

$^{13}$C NMR (125 MHz, $CD_2Cl_2$, 25° C.): δ=147.6; 138.0; 137.2; 135.3; 128.6; 126.2; 125.2; 124.8; 123.6; 84.7; 83.6; 25.2 ppm;

IR (KBr): ν ($cm^{-1}$)=2990, 2932, 2365, 2341, 1526, 1347, 1300, 1149, 1126, 788; UV-Vis ($CHCl_3$): $\lambda_{max}$ (ε)=333 nm (4290 $M^{-1}$ $cm^{-1}$);

MS (FD): m/z (rel. int.)=299.6 (100%) [$M^+$].

b) Preparation of N-(2,6-diisopropylphenyl)-1,6-bis[4-(1,1,3,3-tetramethylbutyl)-phenoxy]-9-(5-nitronaphthyl)perylene-3,4-dicarboximide V'

First a solution of 0.69 g (5.0 mmol) of potassium carbonate in 20 ml of water and 2 ml of ethanol and then 0.06 g (0.051 mmol) of tetrakis(triphenylphosphine)palladium(0) were added to a mixture, stirred under argon, of 1.05 g (1.09 mmol) of N-(2,6-diisopropylphenyl)-1,6-bis[4-(1,1,3,3-tetramethylbutyl)phenoxy]-9-bromoperylene-3,4-dicarboximide IIIa', 1.03 g (3.44 mmol) of 1-(4,4,5,5-tetramethyl-1,3,2-dioxaboran-2-yl)-5-nitronaphthalene IVb' and 40 ml of toluene. Subsequently, the mixture was heated to 80° C. under argon and stirred at this temperature for 16 h. After cooling to room temperature, the organic phase was removed and the solvent was removed under reduced pressure. The crude product was subjected to column chromatography on silica gel with a 1:1 mixture of toluene and hexane as the eluent.

1.15 g of V' were obtained in the form of a red solid, which corresponds to a yield of 100%.

Analytical Data:

Melting point: 202° C.; Elemental analysis ($C_{72}H_{72}N_2O_6$) (% by weight calc./found): C, 81.48/81.53; H, 6.84/7.02; N, 2.64/2.70;

$^1$H NMR (500 MHz, $CD_2Cl_2$, 25° C.): δ=9.50 (d, 1H, J=8.2 Hz); 9.38 (dd, 1H, J=6.6 and 2.2 Hz); 8.62 (d, 1H, J=8.9 Hz); 8.28 (d, 2H, J=3.2 Hz); 8.18 (dd, 1H, J=7.6 and 1.0 Hz); 7.77-7.65 (m, 3H); 7.49 (d, 1H, J=7.9 Hz); 7.39-7.11 (m, 10H); 7.00 (dd, 4H, J=11.7 and 8.4 Hz); 2.75 (sep, 2H, J=6 Hz); 1.76 (d, 4H, J=2.5 Hz); 1.40 (d, 12H, J=2.2 Hz); 1.13 (dd, 12H, J=6.6 and 1.9 Hz); 0.75 ppm (d, 18H, J=2.2 Hz);

$^{13}$C NMR (Spinecho, 125 MHz, $CD_2Cl_2$, 25° C.): δ=163.7; 163.5; 154.6; 154.4; 153.7; 147.7; 147.1; 147.0; 146.5; 140.0; 139.2; 134.1; 133.3; 132.2; 133.1; 131.6; 130.1; 129.8; 129.7; 129.4; 129.2; 120.0; 128.6; 128.5; 128.4; 127.3; 127.0; 125.7; 125.0; 124.4; 124.3; 124.2; 124.1; 123.5; 123.4; 122.2; 119.0; 118.8; 57.5; 32.7; 31.7; 30.1; 29.5; 29.3; 24.2; 23.2; 23.1 ppm;

IR (KBr): ν ($cm^{-1}$)=2963, 2869, 2365, 2341, 1708, 1669, 1600, 1530, 1499, 1322, 1273, 1207, 1168, 877, 792; UV-Vis ($CHCl_3$): $\lambda_{max}$ (ε)=517 (42030), 486 (27590), 420 (790), 345 (7790), 276 (34430) nm ($M^{-1}$ $cm^{-1}$);

Fluorescence ($CHCl_3$): $\lambda_{max}$=574 nm;

MS (FD): m/z (rel. int.)=1060.3 (100%) [$M^+$].

c) Preparation of N-(2,6-diisopropylphenyl)-1,6-bis[4-(1,1,3,3-tetramethylbutyl)-phenoxy]-11-nitroterrylene-3,4-dicarboximide VIa'

A solution of 1.0 g (0.94 mmol) of V', 1.17 g (9.42 mmol) of 1,5-diazabicyclo[4.3.0]non-5-ene and 0.45 g (4.7 mmol) of sodium tert-butoxide in 7 ml of diethylene glycol dimethyl ether in a 25 ml Schlenk tube was purged with argon, heated to 70° C. and stirred at this temperature for 2 h. After cooling to 40° C., the reaction product was precipitated with 100 ml of water, filtered off, washed with water and dried. Even though the crude product can be used directly without further purification for the subsequent step, it was subjected to analytical purposes to column chromatography on silica gel with a 4:1 mixture of methylene chloride and hexane as the eluent.

0.35 g of VIa' was obtained in the form of a blue solid, which corresponds to a yield of 35%.

Analytical Data:

Melting point: 363° C.;

Elemental analysis ($C_{72}H_{70}N_2O_6$) (% by weight calc./found): C, 81.63/80.78; H, 6.66/6.64; N, 2.64/2.58;

$^1$H NMR (500 MHz, $CD_2Cl_2$, 25° C.): δ=9.13 (dd, 2H, J=10.0 and 8.5 Hz); 8.20 (d, 2H, J=7.0 Hz); 8.25 (d, 1H, J=8.5 Hz); 7.98 (m, 2H); 7.92 (m, 2H); 7.85 (d, J=8.5 Hz); 7.48 (m, 6H); 7.34 (d, 2H, J=7.9 Hz); 7.10 (dd, 4H, J=8.5 and 6.4 Hz); 2.78 (sep, 2H, J=6.7 Hz); 1.76 (s, 4H); 1.40 (s, 12H); 1.14 ppm (d, 12H, J=7.0 Hz);

$^{13}$C NMR (Spinecho, 125 MHz, $CD_2Cl_2$, 25° C.): δ=163.5; 154.7; 154.5; 153.7; 153.6; 147.3; 147.2; 146.5; 145.2; 136.4; 131.6; 131.4; 131.0; 130.9; 129.9; 129.8; 129.6; 129.4; 129.1; 128.6; 128.3; 128.0; 127.3; 126.7; 126.6; 126.3; 125.2; 124.4; 124.1; 124.0; 123.9; 123.5; 122.9; 122.6; 122.5; 122.2; 119.7; 118.6; 57.4; 38.7; 32.7; 32.3; 31.9; 31.7; 30.1; 29.8; 29.5; 24.2; 23.1; 14.3;

IR (KBr): ν ($cm^{-1}$)=2959, 2873, 2365, 2341, 1708, 1677, 1603, 1584, 1502, 1324, 1281, 1211, 1173, 811; UV-Vis ($CHCl_3$): $\lambda_{max}$ (ε)=643 (82900), 598 (49160), 445 (6680), 279 (39450) nm ($M^{-1}$ $cm^{-1}$);

Fluorescence ($CHCl_3$): $\lambda_{max}$=702 nm;

MS (FD): m/z (rel. int.)=1059.6 (100%) [$M^+$].

d) Preparation of N-(2,6-diisopropylphenyl)-1,6-bis [4-(1,1,3,3-tetramethylbutyl)-phenoxy]-11-aminoterrylene-3,4-dicarboximide VIb'

700 mg (12.5 mmol) of iron powder were added to a solution of 2.0 g (0.95 mmol) of VIa' in 300 ml of ethanol. After dropwise addition of 20 ml of concentrated hydrochloric acid, the mixture was heated to reflux temperature and stirred at this temperature for 1 h. After cooling to room temperature, the reaction solution was passed through a suction filter to remove the undissolved iron powder. The iron powder was washed repeatedly with methylene chloride. The organic phase was removed from the filtrate, and the solvent was removed under reduced pressure.

0.80 g of VIb' was obtained in the form of a dark blue solid, which corresponds to a yield of 92%.

Analytical Data:

MS (FD): m/z (rel. int.)=1029.1 (100%) [M$^+$].

e) Preparation of N-(2,6-diisopropylphenyl)-1,6-bis [4-(1,1,3,3-tetramethylbutyl)-phenoxy]-11-iodoterrylene-3,4-dicarboximide VIc'

29 ml of 4.5 M hydrochloric acid was slowly added dropwise to a solution of 0.65 g (0.63 mmol) of VIb' in a mixture of 8 ml of diethyl ether, 6 ml of tetrahydrofuran and 1 ml of acetonitrile. After cooling to from −5 to −10° C., a solution of 4.0 g (58.0 mmol) of sodium nitrite in 8 ml of acetonitrile and 12 ml of water was added dropwise over a period 15 min at such a rate that the temperature did not rise above −5° C. After stirring at this temperature for a further 30 minutes, the reaction solution was added to a cooled mixture of 10.0 g (66.7 mmol) of sodium iodide, 66 ml of acetonitrile and 33 ml of water, stirred at 0° C. for a further 2 hours and then warmed slowly to room temperature. The organic phase obtained by extraction with methylene chloride was washed first with sodium sulfite solution and then with water, then the methylene chloride was removed under reduced pressure. The crude product was filtered briefly through silica gel, washed with methylene chloride, dried under reduced pressure and used without further purification in step f).

0.12 g of VIc' was obtained in the form of a blue solid, which corresponds to a yield of 17%.

Analytical Data:

MS (FD): m/z (rel. int.)=1140 (100%) [M$^+$].

f) Preparation of bis[N-(2,6-diisopropylphenyl)-1,6-bis[4-(1,1,3,3-tetramethyl-butyl)phenoxy]terrylene-3,4-dicarboximide] VII'

First, N-(2,6-diisopropylphenyl)-1,6-bis[4-(1,1,3,3-tetramethylbutyl)phenoxy]-11-(4,4,5,5-tetramethyl-1,3,2-dioxaboran-2-yl)terrylene-3,4-dicarboximide VId' was prepared as follows:

34 mg (0.15 mmol) of bis(pinacolato)diborane, 34 mg (0.30 mmol) of potassium acetate and 10 mg (0.03 mmol) of [1,1'-bis(diphenylphosphino)ferrocene]palladium(II) chloride were added successively to a solution of 100 mg (0.09 mmol) of VIc' in 10 ml of toluene in a 50 ml Schlenk tube. The resulting mixture was then heated to 60° C. under argon and kept at this temperature overnight. After cooling to room temperature, the solvent was distilled off. The solid residue was subjected to column filtration on silica gel with methylene chloride as the eluent.

0.08 g of VId' was obtained in the form of a dark blue solid, which corresponds to a yield of 78%.

The resulting VId' was used without further purification to prepare bis[N-(2,6-diisopropylphenyl)-1,6-bis[4-(1,1,3,3-tetramethylbutyl)phenoxy]terrylene-3,4-dicarboximide] VII'.

First a solution of 0.027 g (0.20 mmol) of potassium carbonate in a mixture of 0.9 ml of water and 0.1 ml of ethanol and then 0.010 g (0.009 mmol) of tetrakis(triphenyl-phosphine)palladium(0) were added to a solution, stirred under argon, of 0.04 g (0.035 mmol) of VIc' and 0.04 g (0.035 mmol) of VId' in 2 ml of dioxane. After purging once again with argon, the mixture was stirred at 70° C. for 24 h. The crude product obtained by distilling off the solvent was subjected to column chromatography on silica gel with a 1:1 mixture of methylene chloride and hexane as the eluent and used without further purification in step g).

0.06 g of VII' was obtained in the form of a blue solid, which corresponds to a yield of 85%.

g) Cyclodehydrogenation to N,N'-bis(2,6-diisopropylphenyl)-1,6,15-20-tetra[4-(1,1,3,3-tetramethylbutyl)phenoxy]hexarylene-3,4:17,18-tetracarboximide Ia'

A mixture of 0.050 g (0.025 mmol) of VII', 0.105 g (0.76 mmol) of potassium carbonate and 3 ml of ethanolamine was purged with argon, heated to 135° C. and stirred at this temperature for 20 h. The reaction product precipitated after cooling to 40° C. by precipitating the reaction solution in water was filtered off, washed with hexane and dried under reduced pressure.

0.42 g of Ia' was obtained in the form of a green solid, which corresponds to a yield of 84%.

Analytical Data:

Melting point: >400° C.

IR (KBr): ν (cm$^{-1}$)=2957, 2360, 2341, 1702, 1666, 1589, 1567, 1537, 1503, 1472, 1409, 1364, 1320, 1279, 1211, 1179, 1105, 1056, 875, 837; UV-Vis (CHCl$_3$): $\lambda_{max}$ ($\epsilon$)=953 nm (293000), 849 (110300), 763 (35500) (M$^{-1}$ cm$^{-1}$)

MS (MALDI-TOF): m/z (rel. int.)=2024.0 (100%) [M$^+$].

Example 2

N,N'-bis(2,6-diisopropylphenyl)-1,6,13,18-tetra[4-(1,1,3,3-tetramethylbutyl)-phenoxy]pentarylene-3,4:15,16-tetracarboximide Ib' a) Preparation of N-(2,6-diisopropylphenyl)-1,6-bis [4-(1,1,3,3-tetramethylbutyl)-phenoxy]-9-(4,4,5,5-tetramethyl-1,3,2-dioxaboran-2-yl)perylene-3,4-dicarboximide IVa'

A solution of 0.97 g (1.0 mmol) of IIIa in 100 ml of toluene was purged with argon. Subsequently, 0.33 g (3.0 mmol) of potassium acetate, 0.34 g (1.5 mmol) of bis(pinacolato)diborane and 0.04 g (0.1 mmol) of [1,1'-bis(diphenylphosphino)ferrocene]palladium(II) chloride were added. After purging once again with argon, the mixture was heated to 80° C. and stirred at this temperature for 16 h. After cooling to room temperature, the solvent was removed. The crude product was subjected to column chromatography on silica gel with methylene chloride as the eluent.

0.67 g of IVa' was obtained in the form of a red solid, which corresponds to a yield of 65%.

Analytical Data:

Melting point: 182° C.;

Elemental analysis (C$_{68}$H$_{78}$BNO$_6$) (% by weight calc./found): C, 80.37/80.16; H, 7.74/7.72; N, 1.38/1.41;

$^1$H NMR (250 MHz, CD$_2$Cl$_2$, 25° C.): δ=9.35 (dd, 1H, J=8.0 Hz); 9.28 (d, 1H, J=8.0 Hz); 8.89 (dd, 1H, J=8.0 Hz); 8.22 (s, 1H); 8.21 (s, 1H); 8.13 (d, 1H, J=8.0 Hz); 7.64 (t, 1H, J=7.5 Hz); 7.40 (m, 5H); 7.30 (d, 2H, J=8.0 Hz); 7.06 (m, 4H); 2.69 (m, 2H); 1.72 (s, 4H); 1.42 (s, 12H); 1.37 (s, 12H); 1.09 (d, 12H, J=7.5 Hz); 0.71 (s, 18H);

$^{13}$C NMR (Spinecho, 62.5 MHz, CD$_2$Cl$_2$, 25° C.): δ=163.6; 154.2; 154.0; 153.7; 146.7; 146.6; 146.4; 137.3; 136.2; 132.2; 131.5; 131.4; 130.3; 129.7; 129.4; 128.9; 128.3; 127.9; 127.8; 127.5; 127.1; 124.6; 124.3; 123.4; 122.3; 121.7; 118.5; 118.3; 84.5; 57.3; 38.5; 32.5; 31.8; 31.6; 29.3; 25.1; 24.0;

IR (KBr): ν (cm$^{-1}$)=2958, 2361, 1707, 1671, 1598, 1503, 1467, 1412, 1329, 1272, 1138, 1013, 872, 770, 676, 579; UV-Vis (CHCl$_3$): λ$_{max}$ (ε)=520 (42060), 490 (27600), 421 (7800) nm (M$^{-1}$ cm$^{-1}$);

MS (FD): m/z (rel. int.)=1015.8 (100%) [M$^+$].

b) Preparation of N-(2,6-diisopropylphenyl-1,6-bis[4-(1,1,3,3-tetramethylbutyl)-phenoxy]-11-(9-[N-(2,6-diisopropylphenyl)]-1,6-bis[4-(1,1,3,3-tetramethylbutyl)-phenoxy]perylene-3,4-dicarboximide) terrylene-3,4-dicarboximide VIII'

First a solution of 0.03 g (0.2 mmol) of potassium carbonate in 0.9 ml of water and 0.1 ml of ethanol and then 0.01 g (0.01 mmol) of tetrakis(triphenyl-phosphine)palladium(0) were added to a mixture, stirred under argon, of 0.09 g (0.92 mmol) of IVa' and 0.06 g (0.05 mmol) of N-(2,6-diisopropylphenyl)-1,6-bis[4-(1,1,3,3-tetramethylbutyl)phenoxy]-11-iodoterrylene-3,4-dicarboximide VIc' in 3 ml of toluene. The mixture was heated to 70° C. under argon and stirred at this temperature for 72 h. After cooling to room temperature, the organic phase was removed and the solvent was removed under reduced pressure. The crude product was subjected to column chromatography on silica gel with a 1:1 mixture of methylene chloride and hexane as the eluent.

16 mg of VIII' were obtained in the form of a red solid, which corresponds to a yield of 17%.

Analytical Data:
MS (FD): m/z (rel. int.)=1902.6 (100%) [M$^+$].

c) Cyclodehydrogenation to N,N'-bis(2,6-diisopropylphenyl)-1,6,13,18-tetra[4-(1,1,3,3-tetramethylbutyl)phenoxy]pentarylene-3,4:15,16-tetracarboximide Ib'

A mixture of 0.016 g (0.008 mmol) of VIII', 0.053 g (0.38 mmol) of potassium carbonate and 2 ml of ethanolamine was purged with argon, heated to 135° C. and stirred at this temperature for 16 h. The reaction product precipitated after cooling to 40° C. by precipitating the reaction solution in 100 ml of water was filtered off, washed with water and dried. The crude product was subjected to column chromatography on silica gel with a 3:2 mixture of methylene chloride and hexane as the eluent.

15 mg of Ib' were obtained in the form of a black-green solid, which corresponds to a yield of 94%.

Analytical Data:
$^1$H NMR (500 MHz, CD$_2$Cl$_2$, 25° C.): δ=9.22 (d, 4H, J=8.5 Hz); 8.21 (s, 4H); 7.99 (m, 8H); 7.47 (t, 2H, J=8.2 Hz); 7.38 (d, 8H, J=8.8 Hz); 7.32 (d, 4H, J=7.6 Hz); 7.03 (d, 8H, J=8.8Hz); 2.78 (sep, 4H, J=6.7 Hz); 1.70 (s, 8H); 1.33 (s, 24H); 1.10 (d, 24H, J=7.1 Hz); 0.72 (s, 36H);

UV-Vis (CHCl$_3$): λ$_{max}$ (ε)=877 (235200), 783 (110300), 763 (91000), 706 (25400) nm (M$^{-1}$ cm$^{-1}$);

MS (FD): m/z (rel. int.)=1900.7 (100%) [M$^+$].

Example 3

N,N'-bis(1-heptyloctyl)pentarylene-3,4:15,16-tetracarboximide Ib'' a) Preparation of N-(1-heptyloctyl)-9-(4,4,5,5-tetramethyl-1,3,2-dioxaboran-2-yl)-perylene-3,4-dicarboximide IVa'

558 mg (2.5 mmol) of bis(pinacolato)diborane, 558 mg (5.3 mmol) of potassium acetate and 44 mg (0.1 mmol) of [1,1'-bis(diphenylphosphino)ferrocene]palladium(II) chloride were added successively to a solution of 1.2 g (2 mmol) of N-(1-heptyloctyl)-9-bromoperylene-3,4-dicarboximide IIIa'' in 20 ml of dioxane in a 50 ml Schlenk tube. The resulting mixture was then heated to 70° C. under argon and kept at this temperature overnight. After cooling to room temperature, the product was extracted with methylene chloride and washed with water. The solvent was then distilled off. The solid residue was subjected to column chromatography on silica gel with methylene chloride as the eluent.

1.0 g of IVa' was obtained in the form of a red solid, which corresponds to a yield of 78%.

Analytical Data:
Melting point: 213° C.;
$^1$H NMR (300 MHz, THF-d$_8$, 25° C.): δ=8.87 (d, 1H, J=7.7 Hz); 8.55-8.47 (m, 6H); 8.15 (d, 1H, J=7.7 Hz); 7.59 (t, 1H, J=7.7 Hz); 5.27-5.17 (m, 1H); 2.40-2.28 (m, 2H); 1.84-1.77 (m, 2H); 1.44 (s, 12H); 1.34-1.24 (m, 20H); 0.85-0.81 (t, 6H, J=6.8 Hz) ppm;

$^{13}$C NMR (75 MHz, THF-d$_8$, 25° C.): δ=165.2; 164.3; 139.0; 137.8; 137.3; 132.8; 132.2; 131.5; 130.6; 130.0; 128.6; 127.8; 127.4; 124.4; 123.3; 123.2; 122.0; 121.9; 121.3; 84.9; 54.5; 33.2; 32.8; 30.5; 30.2; 27.8; 23.5; 14.4 ppm;

IR (KBr): ν (cm$^{-1}$)=2925, 2854, 2362, 2337, 1691, 1653, 1592, 1507, 1461, 1416, 1376, 1332, 1272, 1246, 1209, 1142, 1113, 1068, 966, 858, 811, 754, 674; UV-Vis (CHCl$_3$): λ$_{max}$ (ε)=514 (47400), 489 (45200) nm (M$^{-1}$ cm$^{-1}$);

Fluorescence (CHCl$_3$): λ$_{max}$=577, 546 nm;
MS (FD): m/z (rel. int.)=657.2 (100%) [M$^+$].

b) Preparation of naphthalene-1,4-bis[N-(1-heptyloctyl)perylene-3,4-dicarboximide] XIIa'

First a solution 0.63 g (4.6 mmol) of potassium carbonate in 20 ml of water and 2 ml of ethanol and then 0.09 g (0.076 mmol) of tetrakis(triphenylphosphine)palladium(0) were added to a mixture, stirred under argon, of 1.00 g (1.52 mmol) of IVa' and 0.22 g (0.76 mmol) of 1,4-dibromonaphthalene IXc' in 40 ml of toluene. Subsequently, the mixture was heated to 80° C. under argon and stirred at this temperature for 16 h. After cooling to room temperature, the organic phase was removed and the solvent was removed under reduced pressure. The crude product was subjected to column chromatography on silica gel with toluene as the eluent.

0.45 g of XIIa' was obtained in the form of a red solid, which corresponds to a yield of 72%.

Analytical Data:
Melting point: 330.5° C.;
$^1$H NMR (500 MHz, THF-d$_8$, 25° C.): δ=8.76 (d, 1H, J=7.7 Hz); 8.75 (d, 1H, J=7.7 Hz); 8.67 (d, 1H, J=8.5 Hz); 8.66 (d, 1H, J=8.5 Hz); 8.60-8.55 (m, 8H); 7.81 (d, 1H, J=6.8 Hz); 7.76 (d, 1H, J=7.7 Hz); 7.73 (d, 1H); 7.68 (d, 1H, J=7.7 Hz); 7.61-7.59 (m, 3H); 7.58 (t, 1H, J=7.7 Hz); 7.50 (t, 1H, J=8.5 Hz); 7.34 (dd, 2H, J=4.3 Hz); 5.24 (m, 2H); 2.33 (m, 4H); 1.85 (m, 4H); 1.38-1.26 (m, 4H); 0.85 (m, 12H) ppm;

$^{13}$C NMR (75 MHz, THF-d$_8$, 25° C.): δ=164.37; 142.15; 139.18; 137.70; 137.58; 134.89; 133.86; 132.53; 131.78; 130.88; 130.69; 130.35; 130.22; 129.25; 128.36; 128.03; 127.54; 127.30; 124.86; 124.41; 123.13; 122.36; 121.54; 121.44; 54.55; 33.25; 32.81; 30.53; 30.21; 27.83; 23.51; 14.40 ppm;

IR (KBr): ν (cm$^{-1}$)=2922, 2852, 2362, 1693, 1652, 1591, 1572, 1504, 1458, 1405, 1351, 1291, 1244, 1170, 1107, 843, 810, 758; UV-Vis (CHCl$_3$): λ$_{max}$ (ε)=521 (91200), 496 (75500), 266 (65400) nm (M$^{-1}$ cm$^{-1}$);

Fluorescence (CHCl$_3$): λ$_{max}$=561 nm;

MS (FD): m/z (rel. int.)=1188.5 (100%) [M$^+$].

c) Cyclodehydrogenation to N,N'-bis(1-heptyloctyl) pentarylene-3,4:15,16-tetracarboximide Ib''

A mixture of 0.10 g (0.084 mmol) of XIIa', 0.09 g (0.67 mmol) of anhydrous aluminum chloride and 2 ml of chlorobenzene was stirred at 75° C. for 20 min. After concentrating the solvent volume under reduced pressure, the remaining liquid was diluted with diethyl ether, and the precipitate was filtered off. The remaining solid was subsequently hydrolyzed with dilute hydrochloric acid, and washed first with water, then with acetone and finally with methylene chloride.

24 mg of Ib' were obtained in the form of a black-green solid, which corresponds to a yield of 24%.

Analytical Data:

Melting point: >400° C.;

IR (KBr): ν (cm$^{-1}$)=2921, 2851, 2362, 1689, 1648, 1591, 1564, 1456, 1386, 1340, 1270, 1210, 1104, 1057, 837, 806; UV-Vis (THF): λ$_{max}$ (ε)=831 (216000), 758 (124600), 673 (59600) nm (M$^{-1}$ cm$^{-1}$);

MS (MALDI-TOF): m/z (rel. int.)=1182.0 (100%) [M$^+$].

Example 4

N,N'-bis(2,6-diisopropylphenyl)-1,6,15,20-tetra[4-(1,1,3,3-tetramethylbutyl)-phenoxy]hexarylene-3,4:17,18-tetracarboximide Ia' a) Preparation of perylene-3,9- and -3,10-bis[N-(2,6-diisopropylphenyl)-1,6-di[4-(1,1,3,3-tetramethylbutyl)phenoxy]perylene-3,4-dicarboximide] X'

A solution of 0.415 g (3.0 mmol) of potassium carbonate in 20 ml of water and 2 ml of ethanol and 0.057 g (0.049 mmol) of tetrakis(triphenylphosphine)palladium(0) were added successively to a solution of 1.0 g (0.98 mmol) of N-(2,6-diisopropylphenyl)-1,6-bis[4-(1,1,3,3-tetramethylbutyl)phenoxy]-9-(4,4,5,5-tetramethyl-1,3,2-dioxaboran-2-yl)perylene-3,4-dicarboximide IVa' and 0.2 g (0.49 mmol) of a mixture of 3,9- and 3,10-dibromoperylene IXa' in 40 ml of toluene. The mixture was heated to 80° C. under argon and stirred at this temperature for 16 h. After cooling to room temperature, the organic phase was removed and the solvent was distilled off under reduced pressure. The crude product was subjected to column chromatography on silica gel with a 1:1 mixture of toluene and hexane as the eluent.

0.99 g of X' was obtained in the form of a red solid, which corresponds to a yield of 79%.

Analytical Data:

Melting point: 300° C.;

$^1$H NMR (700 MHz, CD$_2$Cl$_2$, 25° C.): δ=9.52 (d, 2H, J=6.73 Hz); 9.40 (dd, 2H, J=4.3 and 3.3 Hz); 8.43 (d, 1H, J=7.8 Hz); 8.38 (d, 1H, J=7.8 Hz); 8.31-8.26 (m, 5H); 7.69-7.67 (m, 4H); 7.60-7.57 (m, 2H); 7.49-7.42 (m, 13H); 7.38-7.36 (m, 4H); 7.33 (d, 4H, J=7.8 Hz); 7.15 (d, 4H, J=6.8 Hz); 7.10 (d, 4H, J=7.3 Hz); 2.74 (sep, 4H, J=6.6 Hz); 1.77 (s, 4H); 1.76 (s, 4H); 1.40 (d, 24H, J=7.1 Hz); 1.14-1.13 (m, 24H); 0.76 (s, 18H); 0.75 (s, 18H);

$^{13}$C NMR (Spinecho, 175 MHz, CD$_2$Cl$_2$, 25° C.): δ=163.7; 154.3; 154.2; 153.8; 147.0; 146.9; 146.5; 141.1; 138.3; 138.2; 134.4; 133.2; 132.2; 131.8; 131.7; 131.6; 131.5; 130.1; 129.7; 129.3; 129.2; 129.1; 128.9; 128.5; 128.4; 128.3; 128.0; 127.6; 127.4; 127.3; 127.1; 127.0; 126.9; 124.5; 124.4; 123.5; 122.1; 122.0; 121.2; 121.0; 120.6; 129.5; 118.8; 118.6; 57.5; 38.7; 38.6; 32.7; 31.9; 31.7; 30.1; 29.5; 24.1;

IR (KBr): ν (cm$^{-1}$)=2957, 2870, 2362, 2336, 1707, 1671, 1598, 1502, 1466, 1412, 1335, 1272, 1210, 1173, 1014, 915, 874, 834, 810; UV-Vis (CHCl$_3$): λ$_{max}$ (ε)=531 (133920), 500 (841009), 454 (38830), 421 (34400) nm (M$^{-1}$ cm$^{-1}$);

Fluorescence (CHCl$_3$): λ$_{max}$=660 nm;

MS (FD): m/z (rel. int.)=2029.6 (100%) [M$^+$].

b) Preparation of N-(2,6-diisopropylphenyl-1,6-bis[4-(1,1,3,3-tetramethylbutyl)-phenoxy]-13-(9-[N-(2,6-diisopropylphenyl)]-1,6-bis[4-(1,1,3,3-tetramethyl-butyl)-phenoxy]perylene-3,4-dicarboximide)quaterrylene-3,4-dicarboximide XI'

A solution of 0.83 g (5.14 mmol) of iron(III) chloride in 4 ml of nitromethane was added dropwise under argon to a solution of 1.3 g (0.64 mmol) of X' in 20 ml of methylene chloride. After a reaction time of 24 h at room temperature, the solvent was removed, and the reaction mixture was admixed with aqueous hydrochloric acid, filtered and washed to neutrality with water. The dried crude product was used directly without further purification for the subsequent step.

0.28 g of XI' was obtained in the form of a brown solid, which corresponds to a yield of 22%.

c) Cyclodehydrogenation to N,N'-bis(2,6-diisopropylphenyl)-1,6,15,20-tetra[4-(1,1,3,3-tetramethylbutyl)phenoxy]hexarylene-3,4:17,18-tetracarboximide Ia'

A mixture of 0.2 g (0.1 mmol) of XI', 0.11 g (0.8 mmol) of potassium carbonate and 4 ml of ethanolamine was heated to 130° C. under argon and stirred at this temperature for 16 h. After cooling to room temperature, the reaction mixture was admixed with 20 ml of water. The precipitate formed was filtered off, washed with water and dried. The crude part was subjected to column chromatography on silica gel with methylene chloride as the eluent.

0.17 g of Ia' was obtained in the form of a green solid, which corresponds to a yield of 87%.

Analytical Data:

Melting point: >400° C.;

IR (KBr): ν (cm$^{-1}$)=2957, 2360, 2341, 1702, 1666, 1589, 1567, 1537, 1503, 1472, 1409, 1364, 1320, 1279, 1211, 1179, 1105, 1056, 875, 837; UV-Vis (CHCl$_3$): λ$_{max}$ (ε)=953 (293000), 849 (110300), 763 (35500) nm (M$^{-1}$ cm$^{-1}$);

MS (MALDI-TOF): m/z (rel. int.)=2024.0 (100%) [M$^+$].

What is claimed is:

1. A rylenetetracarboximide of the general formula I

I in which the variables are defined as follows:

R are identical or different radicals:
  hydrogen;

$C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;

$C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;

aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_8$-alkyl, $C_1$-$C_{18}$-alkoxy or cyano, and to which further 5- to 7-membered saturated or unsaturated rings may be fused, which may comprise —O—, —S—, —NR$^1$—, —CO— and/or —SO$_2$— as ring members and/or be substituted by one or more identical or different R$^2$ radicals;

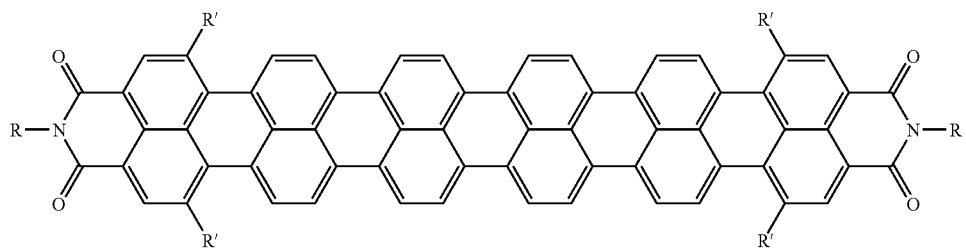

Ia

R' are identical or different radicals:
hydrogen;
aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;
R$^1$ is hydrogen or $C_1$-$C_{18}$-alkyl;
R$^2$, R$^3$ are each independently hydrogen;
$C_1$-$C_{18}$-alkyl, which may be substituted by $C_1$-$C_6$-alkoxy, halogen, hydroxyl, carboxyl and/or cyano; aryl or hetaryl, each of which may be substituted by the aforementioned radicals specified for alkyl and by $C_1$-$C_6$-alkyl;
n is 1 or 2.

2. The rylenetetracarboximide of the general formula I according to claim 1, in which the variables are defined as follows:
R are identical radicals:
hydrogen;
$C_1$-$C_{30}$-alkyl, whose carbon chain may be interrupted by one or more —O— and/or —CO— moieties and which may be mono- or polysubstituted by cyano, $C_1$-$C_6$-alkoxy, aryl, which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;
$C_5$-$C_8$-cycloalkyl which may be mono- or polysubstituted by $C_1$-$C_6$-alkyl;
phenyl, naphthyl, pyridyl or pyrimidyl, each of which may be mono- or polysubstituted by $C_1$-$C_{18}$-alkyl, $C_1$-$C_6$-alkoxy, cyano, nitro, halogen, —CONR$^2$R$^3$, —SO$_2$R$^2$ and/or phenyl- or naphthylazo, each of which may be substituted by $C_1$-$C_{10}$-alkyl, $C_1$-$C_6$-alkoxy or cyano;

R' are identical radicals:
hydrogen; bromine;
phenoxy, phenylthio, pyridyloxy, pyrimidyloxy, pyridylthio or pyrimidylthio, each of which may be mono- or polysubstituted by $C_1$-$C_{12}$-alkyl or $C_1$-$C_{12}$-alkoxy;
R$^1$ is hydrogen or $C_1$-$C_6$-alkyl;
R$^2$, R$^3$ are each independently hydrogen;
$C_1$-$C_{18}$-alkyl, which may be substituted by $C_1$-$C_6$-alkoxy, halogen, hydroxyl, carboxyl and/or cyano; aryl or hetaryl, each of which may be substituted by the aforementioned radicals specified for alkyl and by $C_1$-$C_6$-alkyl;
n is 1 or 2.

3. A process for preparing hexarylenetetracarboximides of the general formula Ia according to claim 1 in which the variables are each as defined in claim 1 except that R' is not hydrogen, wherein said process comprises
a) reacting a diborane of the general formula II

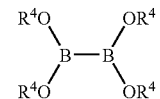

II in which the R$^4$ radicals are the same or different and are each independently hydrogen, $C_1$-$C_{30}$-alkyl, $C_5$-$C_8$-cycloalkyl, aryl or hetaryl, where the R$^4$ radicals disposed in each case on one boron atom may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups,
in the presence of an aprotic organic solvent, of a transition metal catalyst and of a base with
a1) a 9-bromoperylene-3,4-dicarboximide of the general formula IIIa

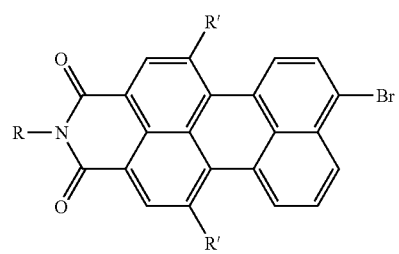

IIIa or
a2) a naphthalene derivative of the general formula IIIb

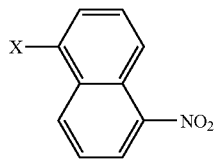

IIIb in which X is halogen, $C_1$-$C_{12}$-alkylsulfonyl, whose alkyl radical may be mono- or polysubstituted by halogen, or $C_6$-$C_{18}$-arylsulfonyl,
b1) subjecting the 9-(dioxaborolan-2-yl)perylene-3,4-dicarboximide of the general formula IVa

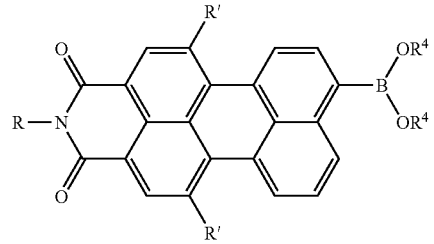

IVa formed in a1), in the presence of an organic solvent, if desired in a mixture with water, and of a transition metal catalyst and of a base, to a Suzuki coupling reaction with a naphthalene derivative IIIb or
b2) subjecting the 1-(dioxaborolan-2-yl)-5-nitronaphthalene of the general formula IVb

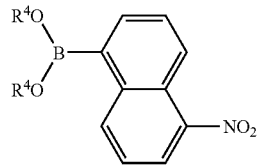

IVb formed in a2), in the presence of an organic solvent, if desired in a mixture with water, and of a transition metal catalyst and of a base, to a Suzuki coupling reaction with a 9-bromoperylene-3,4-dicarboximide IIIa,
c) subjecting the 9-(5-nitronaphthyl)perylene-3,4-dicarboximide of the general formula V

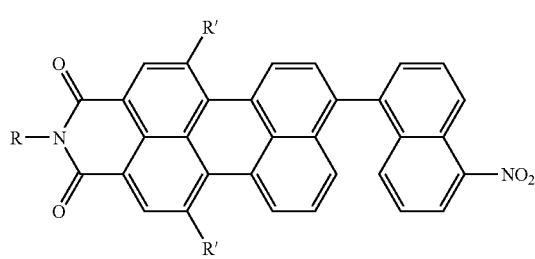

V formed in b1) or b2) to a cyclodehydrogenation in the presence of a base-stable, high-boiling organic solvent and of an alkali metal- or alkaline earth metal-containing base and of a nitrogen-containing auxiliary base,
d) reducing the 11-nitroterrylene-3,4-dicarboximide of the general formula VIa

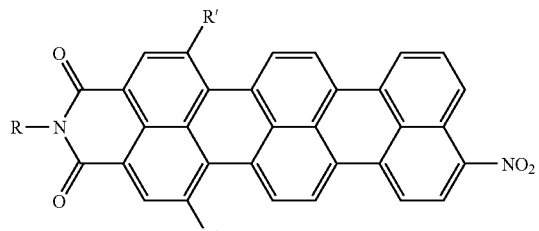

VIa formed in c) with nascent hydrogen,
e) diazotizing the 11-aminoterrylene-3,4-dicarboximide of the general formula VIb

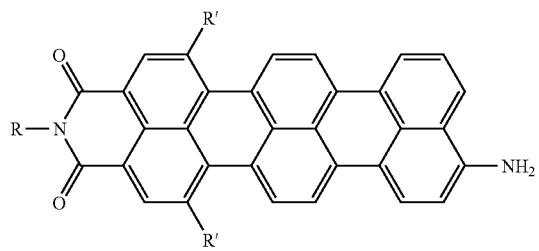

VIb formed in d) and reacting the diazonium salt formed with a metal bromide or iodide,
f) coupling the 11-haloterrylene-3,4-dicarboximide of the general formula VIc

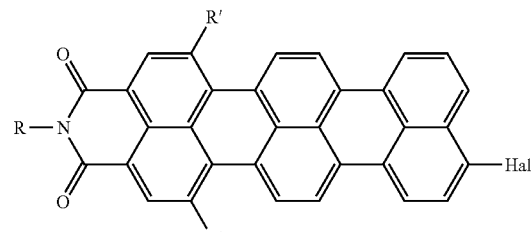

VIc in which Hal is bromine or iodine, formed in e), f1) in the presence of an organic transition metal complex as a catalyst, of free ligand molecules and of an aprotic solvent to give a bisterrylene derivative of the general formula VII

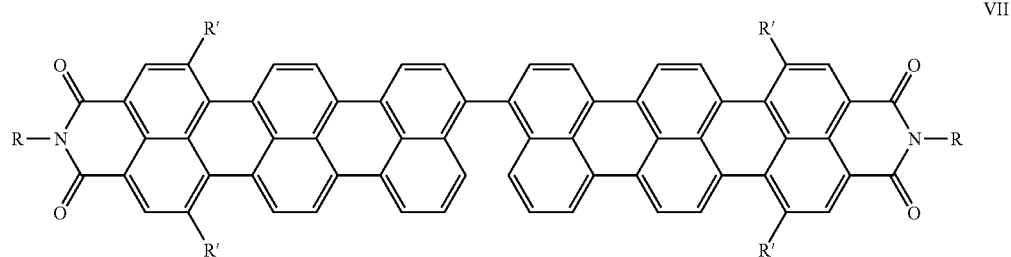

or f2) in the presence of from 30 to 70 mol %, based on the 11-haloterrylene-3,4-dicarboximide VIc, of a diborane II, of a transition metal catalyst, of a base and of an aprotic organic solvent, without intermediate isolation of the 11-(dioxaborolan-2-yl)terrylene-3,4-dicarboximide of the general formula VId

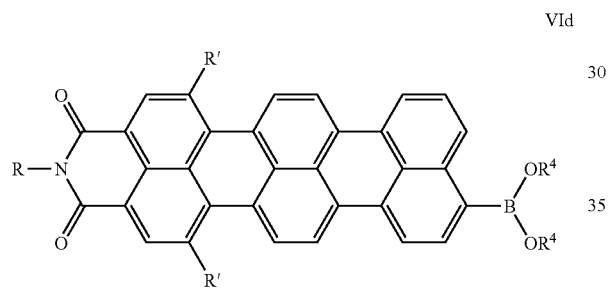

formed in situ, converting it by a Suzuki coupling reaction to the bisterrylene derivative VII and g) converting the bisterrylene derivative VII by cyclodehydrogenation, g1) in an organic reaction medium having hydroxyl and amino functions and comprising a substantially undissolved base or g2) in the presence of a base-stable, high-boiling organic solvent and of an alkali metal- or alkaline earth metal-containing base and of a nitrogen-containing auxiliary base, to the hexarylenetetracarboximide Ia.

4. A process for preparing hexarylenetetracarboximides of the general formula Ia according to claim 1 in which the variables are each as defined in claim 1 except that R' is not hydrogen, wherein said process comprises a) reacting a diborane of the general formula II

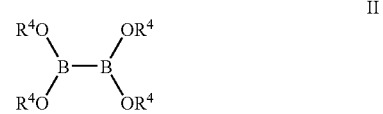

in which the R⁴ radicals are the same or different and are each independently hydrogen, $C_1$-$C_{30}$-alkyl, $C_5$-$C_8$-cycloalkyl, aryl or hetaryl, where the R⁴ radicals disposed in each case on one boron atom may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups, in the presence of an aprotic organic solvent, of a transition metal catalyst and of a base with an 11-haloterrylene-3,4-dicarboximide of the general formula VIc

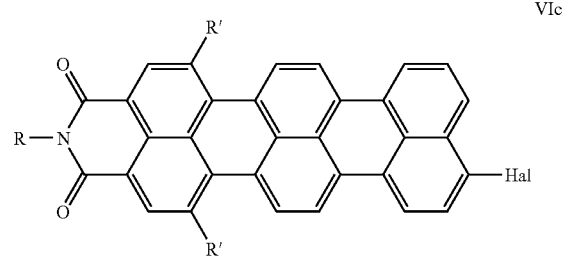

in which Hal is bromine or iodine,

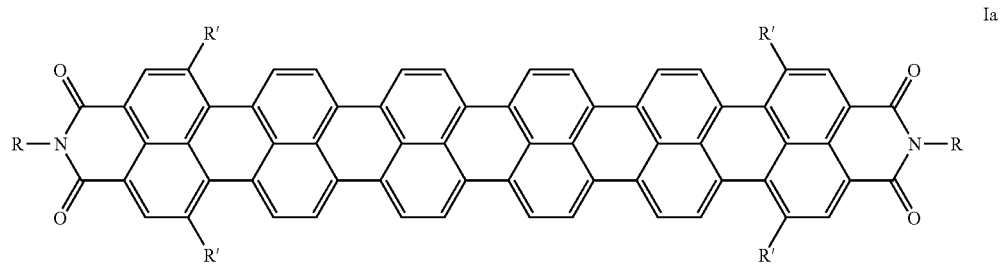

b) subjecting the 11-(dioxaborolan-2-yl)terrylene-3,4-dicarboximide of the general formula VId

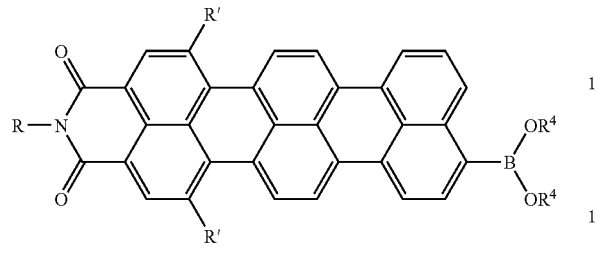

VId formed in a), in the presence of an organic solvent, if desired in a mixture with water, and of a transition metal catalyst and of a base, to a Suzuki coupling reaction with an 11-haloterrylene-3,4-dicarboximide VIc and c) converting the bisterrylene derivative of the general formula VII

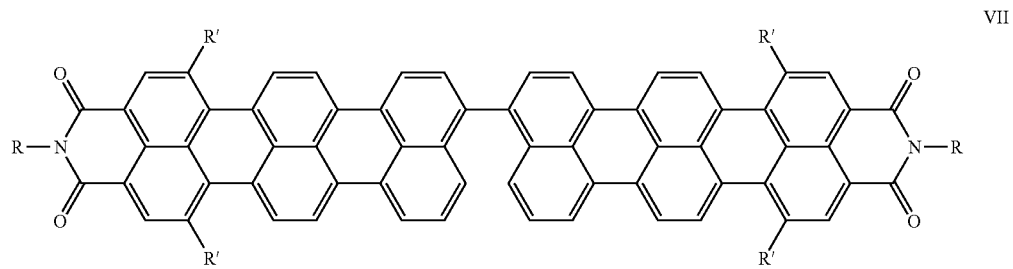

VII formed in b) by cyclodehydrogenation,
c1) in an organic reaction medium having hydroxyl and amino functions and comprising a substantially undissolved base or
c2) in the presence of a base-stable, high-boiling organic solvent and of an alkali metal- or alkaline earth metal-containing base and of a nitrogen-containing auxiliary base,
to the hexarylenetetracarboximide Ia.

5. A process for preparing pentarylenetetracarboximides of the general formula Ib according to claim 1 in which the variables are as defined in claim 1 except that R' is not hydrogen, wherein said process comprises a) subjecting an 11-haloterrylene-3,4-dicarboximide of the general formula VIc

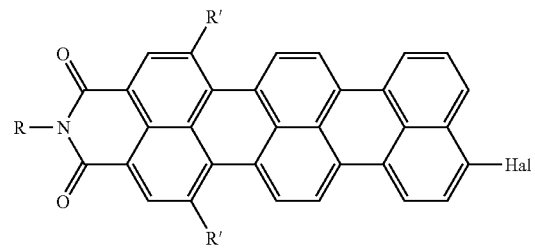

VIc in which Hal is bromine or iodine, in the presence of an organic solvent, if desired in a mixture with water, and also of a transition metal catalyst and of a base, to a Suzuki coupling reaction with a 9-(dioxaborolan-2-yl)perylene-3,4-dicarboximide of the general formula IVa IVa Ib in which the R⁴ radicals are the same or different and are each independently hydrogen, $C_1$-$C_{30}$-alkyl, $C_5$-$C_8$-cycloalkyl, aryl or hetaryl, where the two R⁴ radicals may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups, and b) converting the 11-(9-perylene-3,4-dicarboximide)terrylene-3,4-dicarboximide of the general formula VIII in which the variables are as defined in claim 1 except that R' is not hydrogen, wherein said process comprises a) subjecting 11-(dioxaborolan-2-yl)terrylene-3,4-dicarboximide of the general formula VId VId

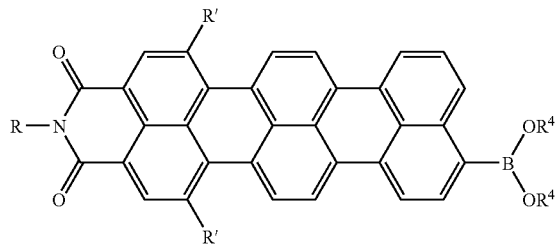

VIII

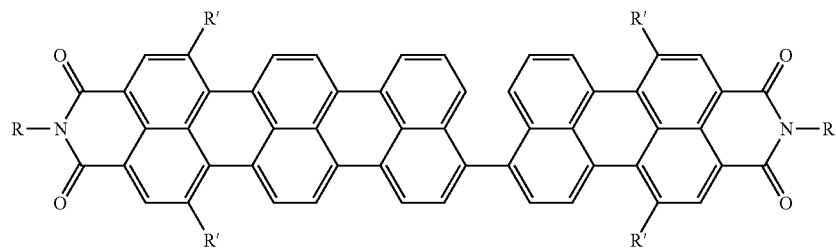

formed in a) by cyclodehydrogenation,
b1) in an organic reaction medium having hydroxyl and amino functions and comprising a substantially undissolved base or
b2) in the presence of a base-stable, high-boiling organic solvent and of an alkali metal- or alkaline earth metal-containing base and of a nitrogen-containing auxiliary base,
to the pentarylenetetracarboximide Ib.

6. A process for preparing pentarylenetetracarboximides of the general formula Ib according to claim 1 in which the R⁴ radicals are the same or different and are each independently hydrogen, $C_1$-$C_{30}$-alkyl, $C_5$-$C_8$-cycloalkyl, aryl or hetaryl, where the two R⁴ radicals may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups, in the presence of an organic solvent, if desired in a mixture with water, and also of a transition metal catalyst and of Ib

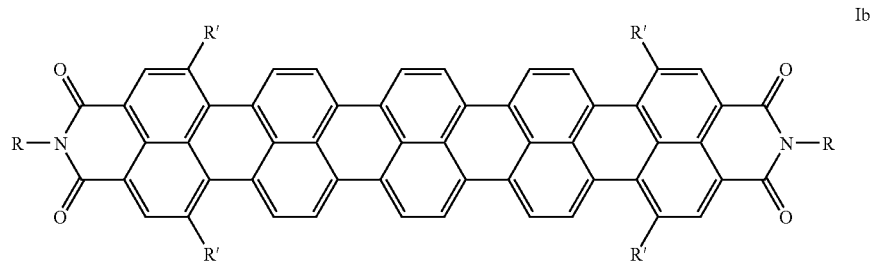

a base, to a Suzuki coupling reaction with a 9-bromoperylene-3,4-dicarboximide of the general formula IIIa

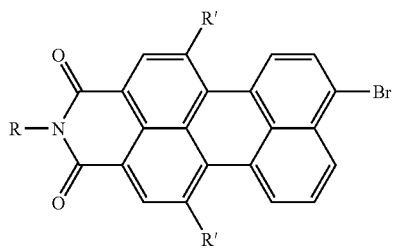

and
b) converting the 11-(9-perylene-3,4-dicarboximide)terrylene-3,4-dicarboximide of the general formula VIII

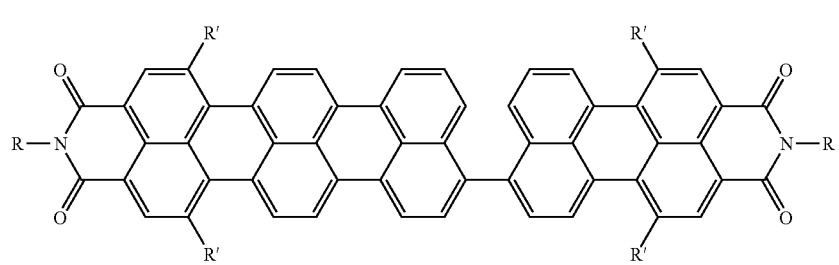

formed in a) by cyclodehydrogenation,
b1) in an organic reaction medium having hydroxyl and amino functions and comprising a substantially undissolved base or
b2) in the presence of a base-stable, high-boiling organic solvent and of an alkali metal- or alkaline earth metal-containing base and of a nitrogen-containing auxiliary base,
to the pentarylenetetracarboximide Ib.

7. A bisterrylene derivative of the general formula VII

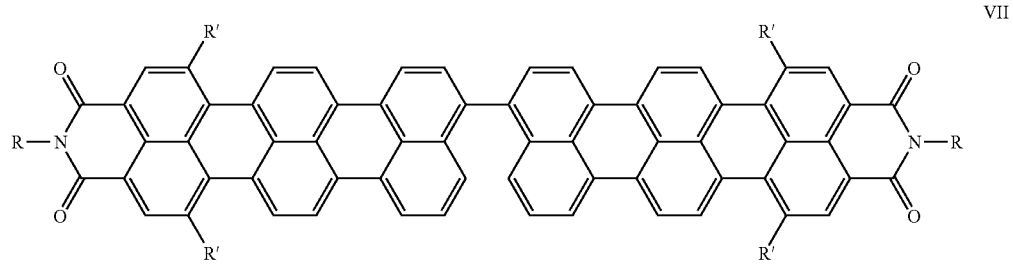

in which the variables are defined as follows:

R are identical or different radicals:
hydrogen;
$C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;

$C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;

aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —NR$^1$—, —CO— and/or —SO$_2$— as ring members and/or be substituted by one or more identical or different R$^2$ radicals;

R' are identical or different radicals:
hydrogen;
aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;

R$^1$ is hydrogen or $C_1$-$C_{18}$-alkyl;

R$^2$, R$^3$ are each independently hydrogen;
$C_1$-$C_{18}$-alkyl, which may be substituted by $C_1$-$C_6$-alkoxy, halogen, hydroxyl, carboxyl and/or cyano;
aryl or hetaryl, each of which may be substituted by the aforementioned radicals specified for alkyl and by $C_1$-$C_6$-alkyl.

8. An 11-(9-perylene-3,4-dicarboximide)terrylene-3,4-dicarboximide of the general formula VIII

VIII

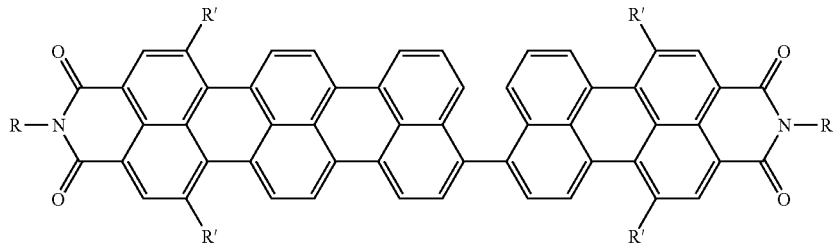

in which the variables are defined as follows:
R are identical or different radicals:
  hydrogen;
  $C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;
  $C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;
  aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —NR$^1$—, —CO— and/or —SO$_2$— as ring members and/or be substituted by one or more identical or different R$^2$ radicals;
R' are identical or different radicals:
  hydrogen;
  aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;
R$^1$ is hydrogen or $C_1$-$C_{18}$-alkyl;
R$^2$, R$^3$ are each independently hydrogen;
  $C_1$-$C_{18}$-alkyl, which may be substituted by $C_1$-$C_6$-alkoxy, halogen, hydroxyl, carboxyl and/or cyano;
  aryl or hetaryl, each of which may be substituted by the aforementioned radicals specified for alkyl and by $C_1$-$C_6$-alkyl.

9. A terrylene-3,4-dicarboximide of the general formula VI

VI

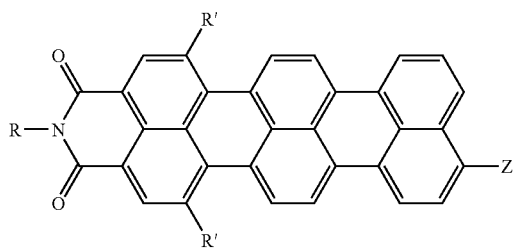

in which the variables are defined as follows:
R are identical or different radicals:
  hydrogen;
  $C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;
  $C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;
  aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —CO— and/or —SO$_2$— as ring members and/or be substituted by one or more identical or different R$^2$ radicals;
R' are identical or different radicals:
  aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;
Z is bromine, iodine, amino, nitro or a radical

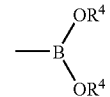

R$^1$ is hydrogen or $C_1$-$C_{18}$-alkyl;
R$^2$, R$^3$ are each independently hydrogen;
  $C_1$-$C_{18}$-alkyl, which may be substituted by $C_1$-$C_6$-alkoxy, halogen, hydroxyl, carboxyl and/or cyano;
  aryl or hetaryl, each of which may be substituted by the aforementioned radicals specified for alkyl and by $C_1$-$C_6$-alkyl;
R$^4$ are identical or different radicals:
  hydrogen, $C_1$-$C_{30}$-alkyl, $C_5$-$C_8$-cycloalkyl, aryl or hetaryl, where the two R$^4$ radicals may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups.

10. A 9-(5-nitronaphthyl)perylene-3,4-dicarboximide of the general formula V

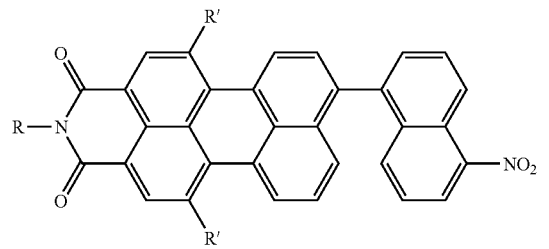

in which the variables are defined as follows:
R are identical or different radicals:
  hydrogen;
  $C_1$-$C_{30}$-alkyl whose carbon chain may be interrupted by one or more —O—, —S—, —$NR^1$—, —CO— and/or —$SO_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may comprise further heteroatoms and be aromatic;
  $C_5$-$C_8$-cycloalkyl whose carbon skeleton may be interrupted by one or more —O—, —S— and/or —$NR^1$— moieties and/or which may be mono- or polysubstituted by $C_1$-$C_{18}$-alkyl;
  aryl or hetaryl, each of which may be mono- or polysubstituted by $C_1$-$C_{18}$-alkyl, $C_1$-$C_{18}$-alkoxy, cyano, nitro, halogen, —$NR^2R^3$, —$CONR^2R^3$, —$SO_2R^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —$NR^1$—, —CO— and/or —$SO_2$— as ring members and/or be substituted by one or more identical or different $R^2$ radicals;
R' are identical or different radicals:
  hydrogen;
  aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —$COOR^1$, —$CONR^2R^3$ and/or —$NHCOR^2$;
$R^1$ is hydrogen or $C_1$-$C_{18}$-alkyl;
$R^2$, $R^3$ are each independently hydrogen;
  $C_1$-$C_{18}$-alkyl, which may be substituted by $C_1$-$C_6$-alkoxy, halogen, hydroxyl, carboxyl and/or cyano;
  aryl or hetaryl, each of which may be substituted by the aforementioned radicals specified for alkyl and by $C_1$-$C_6$-alkyl.

11. A process for preparing hexarylenetetracarboximides of the general formula Ia according to claim 1 in which the variables are each as defined in claim 1, which comprises a) reacting a diborane of the general formula II

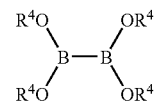

in which the $R^4$ radicals are the same or different and are each independently hydrogen, $C_1$-$C_{30}$-alkyl, $C_5$-$C_8$-cycloalkyl, aryl or hetaryl, where the $R^4$ radicals disposed in each case on one boron atom may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups, in the presence of an aprotic organic solvent, of a transition metal catalyst and of a base with a1) a 9-bromoperylene-3,4-dicarboximide of the general formula IIIa

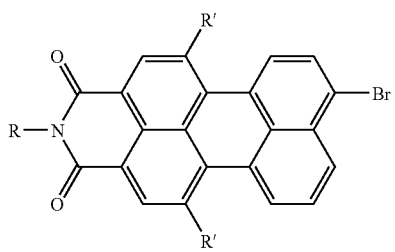

or a2) a dihaloperylene of the general formula IXa

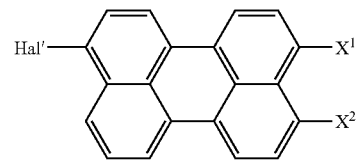

in which Hal' is chlorine or bromine and one of the two $X^1$ and $X^2$ radicals is likewise Hal' and the other radical is hydrogen,

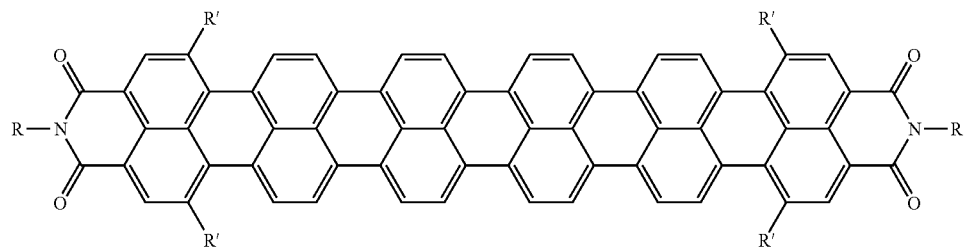

b1) subjecting the 9-(dioxaborolan-2-yl)perylene-3,4-dicarboximide of the general formula IVa

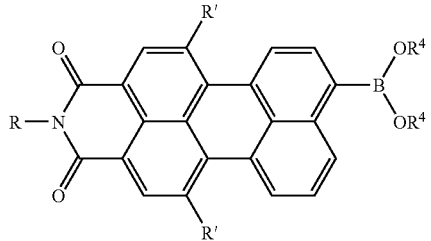

IVa formed in a1), in the presence of an organic solvent, if desired in a mixture with water, and of a transition metal catalyst and of a base, to a Suzuki coupling reaction with a dihaloperylene IXa in a molar ratio of from 2:1 to 6:1 or b2) subjecting the bis(dioxaborolan-2-yl)perylene of the general formula IXb

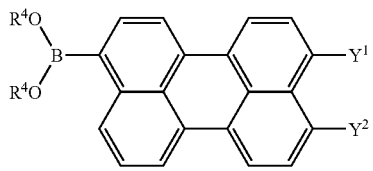

IXb formed in a2), in which one of the two $Y^1$ and $Y^2$ radicals is likewise a radical

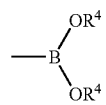

and the other radical is hydrogen, in the presence of an organic solvent, if desired in a mixture with water, and also of a transition metal catalyst and of a base, to a Suzuki coupling reaction with a 9-bromoperylene-3,4-dicarboximide IIIa in a molar ratio of from 1:2 to 1:6 and c) subjecting the perylene-3,9-bis(perylene-3,4-dicarboximide) of the general formula Xa

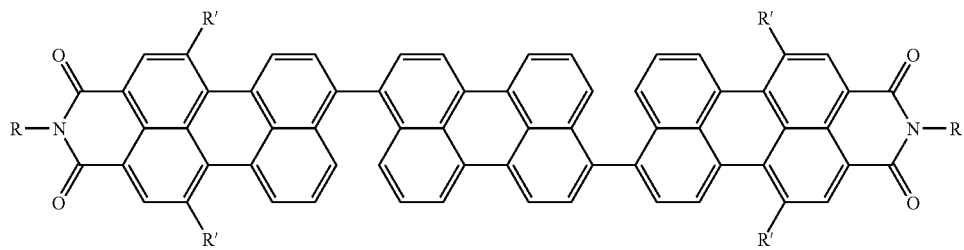

Xa or perylene-3,10-bis(perylene-3,4-dicarboximide) of the general formula Xb

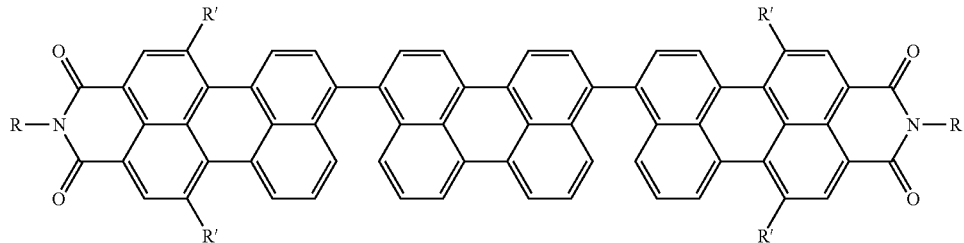

Xb formed in b1) or b2)

c1) to a single-stage cyclodehydrogenation in the presence of a strong Lewis acid and of an inert organic solvent directly to give the hexarylenetetracarboximide Ia or c2a) contacting it with a weak Lewis acid in a first step at room temperature in the presence of an inert organic solvent and c2b) then, after intermediate isolation, in a second, further cyclodehydrogenating the thus formed 13-(9-perylene-3,4-dicarboximide)quaterrylene-3,4-dicarboximide of the general formula XI in which the R⁴ radicals are the same or different and are each independently hydrogen, $C_1$-$C_{30}$-alkyl, $C_5$-$C_s$-cycloalkyl, aryl or hetaryl, where the R⁴ radicals disposed in each case on one boron atom may also be joined together to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups, in the presence of an aprotic organic solvent, of a transition metal catalyst and of a base with

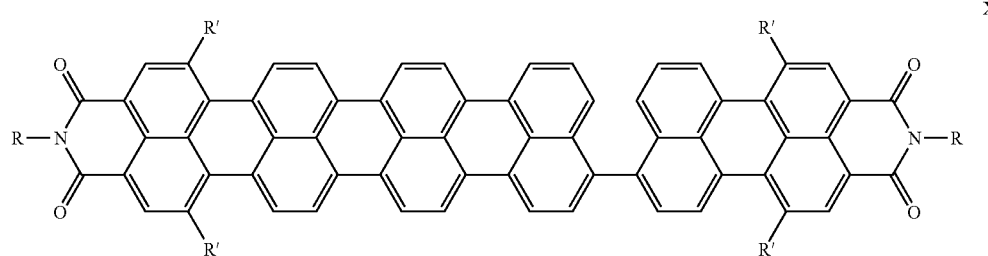

XI c2bα) in an organic reaction medium having hydroxyl and amino functions and comprising a substantially undissolved base or c2bβ) in the presence of a base-stable, high-boiling organic solvent and of an alkali metal- or alkaline earth metal-containing base and of a nitrogen-containing auxiliary base to the hexarylenetetracarboximide Ia.

12. A process for preparing pentarylenetetracarboximides of the general formula Ib according to claim 1 a1) a 9-bromoperylene-3,4-dicarboximide of the general formula IIIa

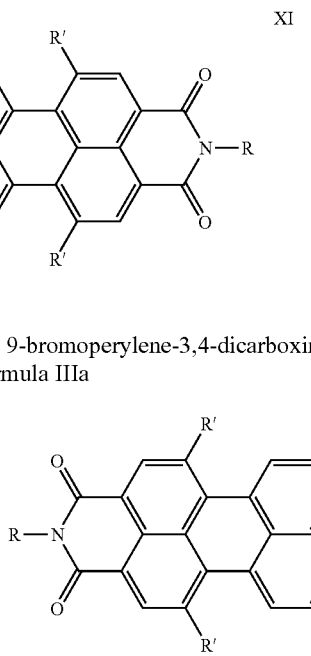

IIIa

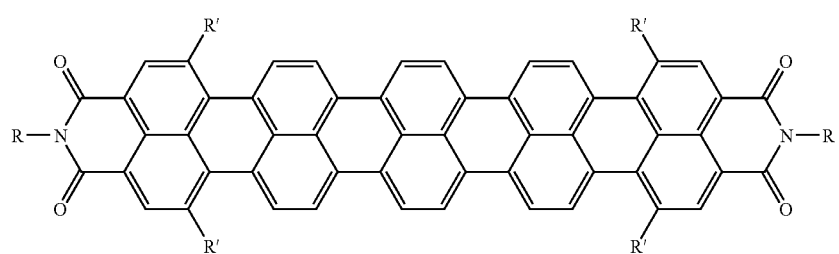

Ib in which the variables are as defined in claim 1, which comprises a) reacting a diborane of the general formula II

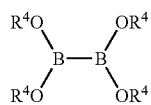

II or a2) a dihalonaphthalene of the general formula IXc

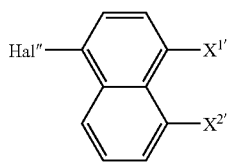

IXc in which Hal" is chlorine, bromine or iodine and one of the two $X^{1'}$ and $X^{2'}$ radicals is likewise Hal" and the other radical is hydrogen, b1) subjecting the 9-(dioxaborolan-2-yl)perylene-3,4-dicarboximide of the general formula IVa

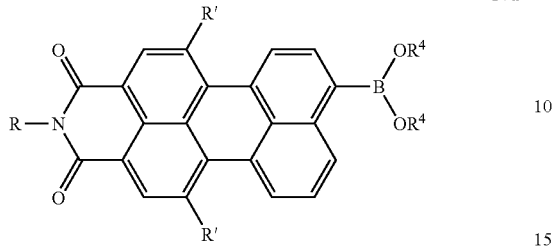

IVa formed in a1), in the presence of an organic solvent, if desired in a mixture with water, and of a transition metal catalyst and of a base, to a Suzuki coupling reaction with a dihalonaphthalene IXc in a molar ratio of from 2:1 to 6:1 or b2) subjecting the bis(dioxaborolan-2-yl)naphthalene of the general formula IXd

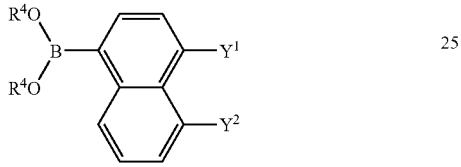

IXd formed in a2), in which one of the two $Y^1$ and $Y^2$ radicals is likewise a radical

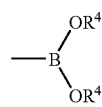

and the other radical is hydrogen, in the presence of an organic solvent, if desired in a mixture with water, and also of a transition metal catalyst and of a base, to a Suzuki coupling reaction with a 9-bromoperylene-3,4-dicarboximide IIIa in a molar ratio of from 1:2 to 1:6 and c) subjecting the naphthalene-1,5-bis(perylene-3,4-dicarboximide) of the general formula XIIa

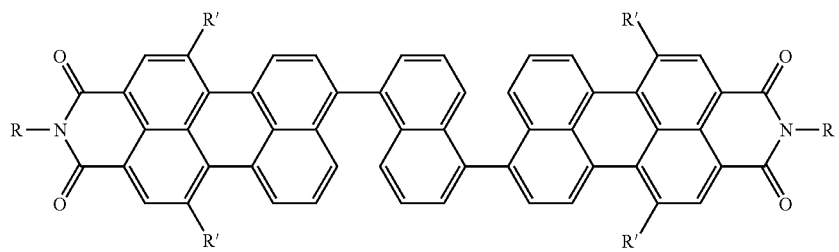

XIIa or naphthalene-1,4-bis(perylene-3,4-dicarboximide) of the general formula XIIb

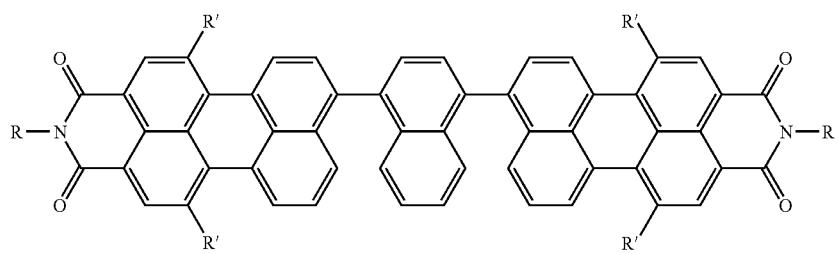

XIIb formed in b1) or b2)
c1) to a single-stage cyclodehydrogenation in the presence of a Lewis acid and of an inert organic solvent directly to give the pentarylenetetracarboximide Ib or
c2a) contacting it with a weak Lewis acid in a first at room temperature in the presence of an inert organic solvent and
c2b) then, after intermediate isolation, in a second, further cyclodehydrogenating the thus formed 11-(9-perylene-3,4-dicarboximide)terrylene-3,4-dicarboximide of the general formula VIII

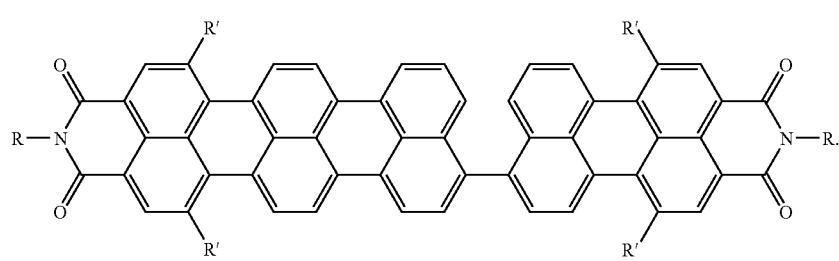

c2bα) in an organic reaction medium having hydroxyl and amino functions and comprising a substantially undissolved base or
c2bβ) in the presence of a base-stable, high-boiling organic solvent and of an alkali metal- or alkaline earth metal-containing base and of a nitrogen-containing auxiliary base
to the pentarylenetetracarboximide Ib.

13. A 13-(9-perylene-3,4-dicarboximide)quaterrylene-3,4-dicarboximide of the general formula XI

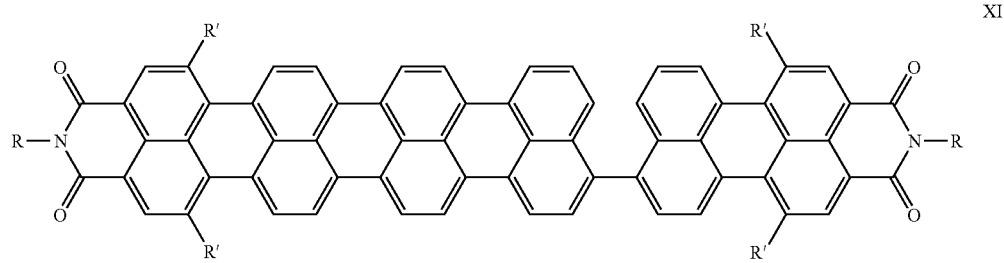

in which the variables are defined as follows:
R are identical or different radicals:
  hydrogen;
  $C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;
  $C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;
  aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —NR$^1$—, —CO— and/or —SO$_2$— as ring members and/or be substituted by one or more identical or different R$^2$ radicals;
R' are identical or different radicals:
  hydrogen;
  aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;

R$^1$ is hydrogen or $C_1$-$C_{18}$-alkyl;

R$^2$, R$^3$ are each independently hydrogen;
  $C_1$-$C_{18}$-alkyl, which may be substituted by $C_1$-$C_6$-alkoxy, halogen, hydroxyl, carboxyl and/or cyano;
  aryl or hetaryl, each of which may be substituted by the aforementioned radicals specified for alkyl and by $C_1$-$C_6$-alkyl.

14. A perylene-3,9-bis(perylene-3,4-dicarboximide) of the general formula Xa

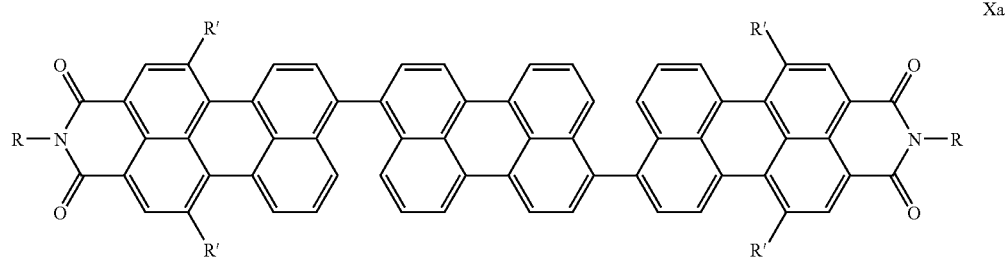

or perylene-3,10-bis(perylene-3,4-dicarboximide) of the general formula Xb

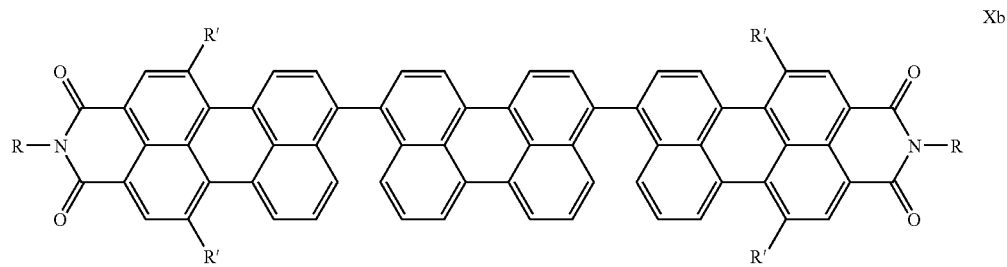

in which the variables are defined as follows:
R are identical or different radicals:
  hydrogen;
  $C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;
  $C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;
  aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_{18}$-alkyl, $C_1$-$C_{18}$-alkoxy or cyano, and to which further 5- to 7-membered saturated or unsaturated rings may be fused, which may comprise —O—, —S—, —NR$^1$—, —CO— and/or —SO$_2$— as ring members and/or be substituted by one or more identical or different R$^2$ radicals;
R' are identical or different radicals:
  hydrogen;
  aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;
$R^1$ is hydrogen or $C_1$-$C_{18}$-alkyl;
$R^2$, $R^3$ are each independently hydrogen;
  $C_1$-$C_{18}$-alkyl, which may be substituted by $C_1$-$C_6$-alkoxy, halogen, hydroxyl, carboxyl and/or cyano;
  aryl or hetaryl, each of which may be substituted by the aforementioned radicals specified for alkyl and by $C_1$-$C_6$-alkyl.

15. A bis(dioxaborolan-2-yl)perylene of the general formula IXb

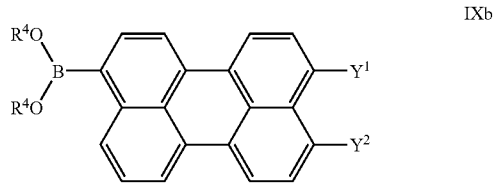

in which the variables are defined as follows:
$R^4$ are identical or different radicals:
  hydrogen, $C_1$-$C_{30}$-alkyl, $C_5$-$C_8$-cycloalkyl, aryl or hetaryl, where the two $R^4$ radicals may also be joined together to form a five-membered ring which optionally have the two oxygen atoms and the boron atom and may be substituted on the carbon atoms by up to 4 $C_1$-$C_{30}$-alkyl, $C_5$-$C_8$-cycloalkyl, aryl or hetaryl groups;
one of the two $Y^1$ and $Y^2$ radicals is likewise a radical

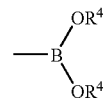

and the other radical is hydrogen.

16. A naphthalene-1,5-bis(perylene-3,4-dicarboximide) of the general formula XIIa

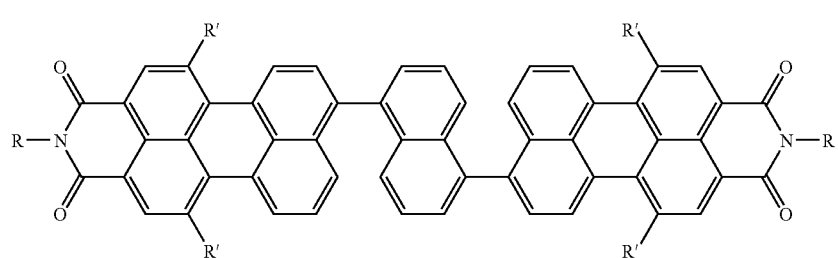

or naphthalene-1,4-bis(perylene-3,4-dicarboximide) of the general formula XIIb

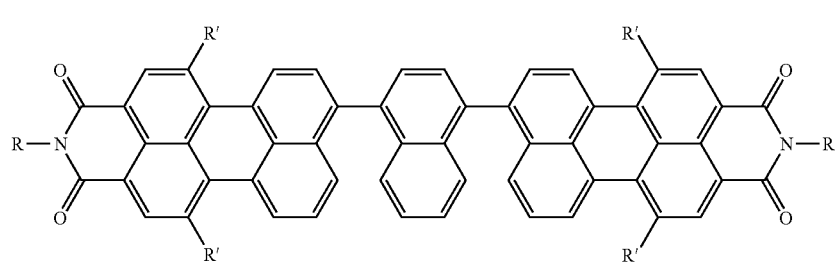

in which the variables are defined as follows:

R are identical or different radicals:
  hydrogen;
  $C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and optionally have further heteroatoms and be aromatic;
  $C_5$-$C_8$-cycloalkyl whose carbon skeleton may be interrupted by one or more —O—, —S— and/or —NR$^1$— moieties and/or which may be mono- or polysubstituted by $C_1$-$C_{18}$-alkyl;
  aryl or hetaryl, each of which may be mono- or polysubstituted by $C_1$-$C_{18}$-alkyl, $C_1$-$C_{18}$-alkoxy, cyano, nitro, halogen, —NR$^2$R$^3$, —CONR$^2$R$^3$, —SO$_2$R$^2$ and/or aryl- or hetarylazo, each of which may be substituted by $C_1$-$C_{18}$-alkyl, $C_1$-$C_{18}$-alkoxy or cyano;

R' are identical or different radicals:
  hydrogen;
  aryloxy, arylthio, hetaryloxy or hetarylthio, each of which may be mono- or polysubstituted by alkyl radicals R, aryl radicals R, $C_1$-$C_{12}$-alkoxy, cyano, halogen, hydroxyl, —COOR$^1$, —CONR$^2$R$^3$ and/or —NHCOR$^2$;

$R^1$ is hydrogen or $C_1$-$C_{18}$-alkyl;
$R^2$, $R^3$ are each independently hydrogen;
  $C_1$-$C_{18}$-alkyl, which may be substituted by $C_1$-$C_6$-alkoxy, halogen, hydroxyl, carboxyl and/or cyano; aryl or hetaryl, each of which may be substituted by the aforementioned radicals specified for alkyl and by $C_1$-$C_6$-alkyl.

17. A composition comprising the rylenetetracarboximides of the formula I according to claim 1.

18. A high molecular weight organic material comprising the rylenetetracarboximides of the formula I according to claim 1.

19. A high molecular weight inorganic material comprising the rylenetetracarboximides of the formula I according to claim 1.

20. A coating composition comprising the rylenetetracarboximides of the formula I according to claim 1.

21. A printer ink composition comprising the rylenetetracarboximides of the formula I according to claim 1.

22. A plastic composition comprising the rylenetetracarboximides of the formula I according to claim 1.

23. An aqueous polymer dispersion comprising the rylenetetracarboximides of the formula I according to claim 1, wherein said aqueous polymer dispersion absorbs in the near infrared region of the electromagnetic spectrum.

24. An inscription comprising the rylenetetracarboximides of the formula I according to claim 1, wherein said inscription absorbs infrared light and is invisible to the human eye.

25. An infrared absorber comprising the rylenetetracarboximides of the formula I according to claim 1.

26. A heat management material comprising the rylenetetracarboximides of the formula I according to claim 1.

27. An infrared laser beam absorbing material comprising the rylenetetracarboximides of the formula I according to claim 1.

28. A plastic fusion treatment material comprising the rylenetetracarboximides of the formula I according to claim 1.

29. A photovoltaic comprising the rylenetetracarboximides of the formula I according to claim 1.

* * * * *